US009526735B2

(12) United States Patent
Kusunoki et al.

(10) Patent No.: US 9,526,735 B2
(45) Date of Patent: Dec. 27, 2016

(54) METHOD FOR SUPPRESSING SURGICAL SITE INFECTION AND COLUMN TO BE USED FOR THE METHOD

(71) Applicant: ASAHI KASEI MEDICAL CO., LTD., Tokyo (JP)

(72) Inventors: Masato Kusunoki, Hyogo (JP); Chikao Miki, Mie (JP); Shigeyuki Yoshiyama, Mie (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 0 days.

(21) Appl. No.: 14/200,733

(22) Filed: Mar. 7, 2014

(65) Prior Publication Data

US 2014/0179659 A1 Jun. 26, 2014

Related U.S. Application Data

(62) Division of application No. 11/572,405, filed as application No. PCT/JP2005/011501 on Jun. 23, 2005, now Pat. No. 8,708,945.

(30) Foreign Application Priority Data

Jul. 22, 2004 (JP) ................................. 2004-213998
Jan. 17, 2005 (JP) ................................. 2005-009201

(51) Int. Cl.
| | | |
|---|---|---|
| A61M 1/36 | (2006.01) | |
| A61K 31/546 | (2006.01) | |
| A61K 31/14 | (2006.01) | |
| A61K 31/43 | (2006.01) | |
| A61K 35/14 | (2015.01) | |

(52) U.S. Cl.
CPC ............. *A61K 31/546* (2013.01); *A61K 31/14* (2013.01); *A61K 31/43* (2013.01); *A61K 35/14* (2013.01); *A61M 1/3679* (2013.01); *A61M 1/3693* (2013.01); *A61M 2202/0439* (2013.01)

(58) Field of Classification Search
None
See application file for complete search history.

(56) References Cited

U.S. PATENT DOCUMENTS

| 4,981,596 | A | 1/1991 | Shiino et al. |
| 5,258,127 | A | 11/1993 | Gsell et al. |
| 5,997,496 | A | 12/1999 | Sekiguchi et al. |
| 7,591,954 | B2 | 9/2009 | Kimura et al. |
| 2003/0152569 | A1 | 8/2003 | Sawada et al. |
| 2004/0228921 | A1 | 11/2004 | Chowdhury et al. |

FOREIGN PATENT DOCUMENTS

| JP | 129855 | 5/1989 |
| JP | 04-240456 | 8/1992 |
| JP | 8-103493 | 4/1996 |
| JP | 2000-217908 | 8/2000 |
| JP | 2001-340453 | 12/2001 |
| JP | 2002-35117 | 2/2002 |
| WO | 2004/050146 | 6/2004 |

OTHER PUBLICATIONS

Adacolumn, Crohn's Disease Forum, retrieved from the internet, Feb. 23, 2016: www.crohnsforum.com/showthread.php?t=15473.*
Medscape, Estimated Blood Volume Calculator, retrieved from the internet Feb. 23, 2016: reference.medscape.com/calculator/estimated-blood-volume.*
Suzuki et al., Selective Granulocyte and Monocyte Adsorptive Apheresis as a First-Line Treatmetn for Steroid Naïve Patients with Active Ulcerative Colities: A Prospective Uncontrolled Study, Digestive Diseases and Sciences, vol. 49, No. 4, Apr. 2004, pp. 565-571.*
S. Yoshiyama et al., "Kaiyosei Daichoen Jutsugo Mobidity Kaizen no Tameno Shukutsuki Hakkekkyu Jokyo Ryoho ni Kansuru Prospective Trial", The Japanese Journal of Gastroenterological Surgery, vol. 37, No. 7, PD-3-06, pp. 240 (2004).
A. Mangram et al., "Guideline for Prevention of Surgical Site Infection", Infection Control and Hospital Epidemiology, vol. 20, No. 4, pp. 247-278 (1999).
Nagao Munenori et al., "Prospective Randmized Study regarding wound infection preventive effect by administration of antibiotics in ileostomy closure surgery", Journal of Japan Society of Coloproctology, vol. 56, No. 9 , Sep. 2003, pp. 663 (#229).
Furukawa Kiyonori et al., "Prophylactic antibiotics therepy in colorectal surgery", Surgery, vol. 63, No. 2, Feb. 1, 2001, pp. 153-156.

(Continued)

*Primary Examiner* — Thane Underdahl
*Assistant Examiner* — Yvonne Pyla
(74) *Attorney, Agent, or Firm* — Greenblum & Bernstein, P.L.C.

(57) ABSTRACT

An object of the present invention is to provide a method for suppressing surgical site infections (SSI) that have occurred at extremely high incidence rates at the time of surgical operations and particularly surgical operations on digestive system organs, and to provide a column to be used for the method. According to the present invention, a method is provided for suppressing surgical site infections, which comprises the steps of: (a) administering a chemotherapeutic drug for treating and/or preventing a surgical site infection; and (b) collecting blood from a surgical subject and removing leukocytes that comprise neutrophils from the blood during or within 24 hours after surgical operation, and then returning the blood from which the leukocytes have been removed to the surgical subject. The present invention also provides a column for blood circulation which is filled with a carrier having affinity for leukocytes comprising neutrophils, which is used for suppressing a surgical site infection during or within 24 hours after surgical operation on a digestive system organ.

8 Claims, 10 Drawing Sheets

(56) References Cited

OTHER PUBLICATIONS

Shibata H, "Cellsorba", Therapeutic Apheresis and Dialysis, vol. 7, No. 1, Feb. 2003, pp. 44-47.
Miki C, "Pouch related complication. Strategies for surgical treatment and a novel concept for prevention", Journal of Japan Society of Coloproctology, vol. 55, No. 9, Sep. 2002, pp. 467 (S2-4).
Japanese Office action that issued with respect to counterpart Japanese Patent Application No. 2005-196011, mail date is Sep. 27, 2011.
Wrenn et al., Perioperative Nursing, 2006, pp. 1-13.
Miki Presentation, 57th Annual Meeting of the Japan Society of Coloproctology (http://plaza.umin.ac.jp/~daiko57/) which was held on Oct. 4, 2002 in Pacifico Yokohama.

* cited by examiner

→●→ Without ELAD (n=54)
→○→ group subjected to therapy immediately after operation (n=9)

- Timing of collection of blood
- 8 times in total : pre-operation (before anesthesia), 2,4,6,8,10 hours after first collection of blood, 1POD

- Items: hematologic, white blood cell fraction

METHOD FOR SUPPRESSING SURGICAL SITE INFECTION AND COLUMN TO BE USED FOR THE METHOD

CROSS-REFERENCE TO RELATED APPLICATIONS

The present application is a divisional of U.S. application Ser. No. 11/572,405, which is a National Stage of International Patent Application No. PCT/JP05/011501 filed Jun. 23, 2005, which claims priority to Japanese Application No. 2139982004 filed Jul. 22, 2004 and Japanese Application No. 0092012005 filed Jan. 17, 2005. The disclosures of U.S. application Ser. No. 11/572,405 and International Patent Application No. PCT/JP05/011501 are incorporated by reference herein in their entireties.

TECHNICAL FIELD

The present invention relates to a method for suppressing surgical site infections that take place after surgical operations on digestive system organs. The present invention further relates to a blood processing method for a surgical subject who has had surgical operation on a digestive system organ, a column to be used for such method, and a chemotherapeutic drug for treating and/or preventing surgical site infections, which is used in combination with the blood processing method.

BACKGROUND ART

The onset of postoperative complications due to infections at surgical sites is a problem when surgical operations are performed. Postoperative infections are classified into surgical site infections (SSI) and remote infections such as pneumonia or urinary tract infections. Surgical site infections mean infections that take place at sites directly subjected to operations. Remote infections mean infections that take place at sites not directly subjected to operations. Furthermore, SSI is further classified as incisional SSI and organ/space SSI. Incisional SSI includes superficial incisional SSI, the onset sites of which are limited to the skin and subcutaneous tissues, and deep incisional SSI, which reaches deeper soft tissues. Furthermore, organ/space SSI means infections of any organs or sites other than incisions that have been subjected to surgical operation (Takashi Yokoyama et al: Prevention of Surgical Site Infection (SSI), Emergency and Intensive Care (*Kyukyu/Shuchuchiryo*) vol. 14 no. 6 2002(6): 637-644).

Regarding etiologic bacteria of these infections, the onset of a surgical site infection is caused by contaminants that exist in the operative fields and are resistant to administered antimicrobial agents. It is generally said that the onset of a remote infection is often caused by antibiotic-resistant bacteria that cause nosocomial infections, such as *Pseudomonas aeruginosa* or methicillin-resistant *Staphylococcus aureus* (MRSA). To prevent postoperative infections and, in particular surgical site infections, a chemotherapeutic drug such as an antibiotic is generally administered for prevention purpose. An important point in this case in terms of prevention of postoperative infections is the targeting of bacteria that can cause intraoperative contamination; that is, indigenous bacteria and contaminants in the operative fields or bacteria that are isolated from resection stumps. Normal bacterial flora significantly differs from organ to organ. The number of bacteria in the upper gastrointestinal tract is generally as few as approximately $10^5$/g because of the effect of gastric hydrochloric acid, while the number of bacteria in the lower digestive tract reaches as high as $10^{11}$ to $10^{12}$/g. Moreover, bacterial species also vary significantly. Gram-positive cocci are the dominant bacterial species in the upper gastrointestinal tract or the respiratory system. Gram-negative bacteria and anaerobic bacteria such as *Bacteroides* and *Lactobacillus* bifidus are the dominant bacterial species in the intestine (Yoshinobu Sumiyama and Yohichi Arima: Preventive Administration of Antimicrobial Agent upon Operation, Emergency and Intensive Care (*Kyukyu/Shuchu Chiryo*) vol. 14, No. 6, 2002(6): 645-650). Therefore, for surgery of the lower digestive tract, for example, drugs such as cephems of the $2^{nd}$ and following generations, which have wide-ranging antibacterial spectra, carbapenem antibiotics, and new quinolone antibiotics are used.

The occurrence frequencies of SSI that occurs after operations on the digestive system, and specifically, of incisional SSI, are extremely high. Inflammatory bowel disease (IBD) is a disease that is treated by operation on the digestive system. Examples of such disease include ulcerative colitis (UC), Crohn's disease (CD), as well as infectious colitis, drug induced colitis, ischemic colitis, radiation colitis, intestinal tuberculosis, and intestinal syphilis. Of these, ulcerative colitis (UC) and Crohn's disease (CD) cases are increasing yearly and are distinguished from other disease cases in view of the frequency of their occurrence.

Ulcerative colitis (UC) is cryptogenic inflammation of the large intestine. Ulcerative colitis is also a diffuse non-specific inflammatory disease that occurs mainly in the large intestine and specifically occurs only between the rectum and the cecum, and it is characterized by continuous lesions. The development sites of such inflammations are limited to mucosa and stratum submucosum. Furthermore, UC is characterized by repeated remission and exacerbation and absence of complete cure.

Regarding ulcerative colitis (UC), elucidation of the amplification mechanism of the inflammation, development of therapeutic methods based on the findings from the elucidation, and development of therapeutic agents for UC are currently being aggressively carried out. For example, leukocyte apheresis (LCAP) using CELLSORBA™, granulocyte apheresis (GCAP) using ADACOLUMN™, or leukocyte apheresis based on centrifugation using an apparatus for collecting blood components has been proven to be effective and is thus recognized as a therapeutic method that is covered by insurance. Furthermore, clinical development tests of anti-CD4 antibodies, anti-TNF-α antibodies, or the like is in progress. However, at actual clinical sites, ulcerative colitis is treated mainly through administration of sulfasalazine (trade name: salazopyrin), which is a sulfa drug and has long been used, RINDERON™ (suppository), or a steroid drug. UC is treated by a combination of such drug administration, nutritional control, psychiatric control, and the like. If such treatment is still ineffective, surgical therapy (surgical operation) is further performed in general.

As described above, the fact that operation on the digestive system often results in the onset of postoperative complications is acknowledged as a problem. For example, the development status of SSI in the past 3 years and 10 months was examined at the medical institution to which the present inventors belong. As a result, the incidence rate of SSI was approximately 20% in the case of operations for gastric cancer, approximately 30% in the case of operations for large bowel cancer, and approximately 33% in the case of operations for rectal cancer, while the incidence rate of SSI was as high as approximately 60% in the case of operations for inflammatory bowel disease including ulcerative colitis.

This may be due to the involvement of immunosuppression status resulting from administration of large amounts of steroids and abnormal conditions resulting from the morbidity of the disease, such as systemic inflammatory response syndrome (SIRS). Actually, when the relationships between the doses of steroids and the incidence rates of postoperative complications were examined, whereas the incidence rate of complications was as high as 65% in the case of a total steroid dose of 7,000 mg or more, the same was approximately only 28% in the case of a total steroid dose of 7,000 mg or less. Moreover, total steroid doses were contrasted with the incidence rates of SSI in the cases of operations for ulcerative colitis. As a result, SSI onset was confirmed at a high level when the total steroid dose administered was more than approximately 15,000 mg, but a significantly low level of SSI onset was confirmed when the same was less than 8,000 mg.

DISCLOSURE OF THE INVENTION

Object to be Achieved by the Invention

An object to be achieved by the present invention is to provide a method for suppressing SSI that take place after surgical operations on digestive system organs, a blood processing method for a surgical subject who has had surgical operation on a digestive system organ, a column to be used for such method, and a chemotherapeutic drug for treating and/or preventing a surgical site infections which is used in combination with the blood processing method.

Means to Achieve the Object

The present inventors have previously focused on and examined the relationship between SSI and various inflammatory cytokines, revealing that blood IL-6 levels are abnormally high after operations for ulcerative colitis, among perioperative inflammatory cytokine levels (Fukunaga T, Kidokoro A, Fukunaga M et al., Kinetics of Cytokines and PMN-E in Thoracoscopic Esophagectomy, Surg Endosc., 2001 Dec. 15(12), 1484-7; and Kikuchi K, Kurokawa H, Matsumoto F, et al., Responses of Cytokines, Acute Phase Proteins, and Polymorphonuclear Cell Elastase to Surgical Stress in the Patients with Esophageal Cancer, Rinsho Byori., 1996 June 44(6), 579-84). Hence, the present inventors have reported that postoperative SIRS can be suppressed as a result of suppression of excessive inflammatory responses through the removal of leukocytes comprising lymphocytes that are cells producing inflammatory cytokines (IL-6) upon operation; that is, through perioperative leukocyte apheresis (perioperative extracorporeal leukocyte apheresis device (ELAD)) (Medical Tribune vol. 36 no. 7 2003/02/13:18-19; and Miki C, Araki T, Yoshiyama S et al., Pouch Related Complication-Strategies for Surgical Treatment and A Novel Concept for Prevention, Journal of Japan Society of Coloproctology, Summary of the 57$^{th}$ Assembly, vol. 55, no. 9 (September, 2002)).

Based on such concept, the present inventors have performed LCAP and GCAP in combination before surgical operations on digestive system organs and particularly for ulcerative colitis, so as to remove inflammatory cytokines, following which they performed operations for ulcerative colitis. As a result, the present inventors have succeeded in suppression of the onset of postoperative complications that take place at high rates after operations for ulcerative colitis. FIGS. 1 and 2 show changes in body temperature and changes in heart rate for comparing cases in which perioperative ELAD was performed with cases in which no such therapy was performed in terms of postoperative inflammatory responses. As described above, the employment of perioperative ELAD in operations for ulcerative colitis suppressed to some extent the onset of postoperative complications. However, the method was not a sufficient method.

The present inventors have focused on fluctuations in perioperative inflammatory cytokine level and granulocyte elastase level in the cases of IBD in order to review the above conventional ELAD protocols. Specifically, the present inventors have examined fluctuations in inflammatory cytokine level and granulocyte elastase level in the presence and the absence of leukocyte apheresis, so as to examine the relationship between the incidence rates of SSI and the presence or the absence of leukocyte apheresis (ELAD). As a result, the patients for whom apheresis had been performed showed significantly decreased blood granulocyte elastase levels, regardless of the presence or the absence of SSI onset. However, the patients who had not been subjected to apheresis and developed SSI showed extremely high blood granulocyte elastase levels.

This fact suggests that the presence or the absence of the onset of postoperative complications is independent of preoperative blood granulocyte elastase levels. Instead, suppression of postoperative blood granulocyte elastase levels leads to the suppression of SSI, so that postoperative complications can be suppressed. Further specifically, extreme inflammatory responses can be more effectively suppressed so as to be able to suppress postoperative systemic inflammatory responses not by performing leukocyte apheresis before operation, as conventionally performed, but by performing leukocyte apheresis (ELAD) during or after operation, when vital reactions due to operative stresses reach their maximum levels. Furthermore, a leukocyte removal method that is employed in the present invention may be not only a filter method based on the extracorporeal circulatory system, but also a centrifugation method or a batch-type method, if necessary. Furthermore, with the combined use of the leukocyte removal method of the present invention and a chemotherapeutic drug, therapeutic effects must be increased because of synergistic effects produced by the combination, and the dose of the chemotherapeutic drug may be decreased.

Furthermore, the present inventors reviewed the conventional ELAD protocols in view of another aspect. The present inventors selected UC patients as patients who are candidates for surgical operations on digestive system organs, and they focused on peripheral blood neutrophils of UC patients. Specifically, the present inventors examined cytokine production in peripheral blood neutrophils isolated from normal subjects and UC patients, to which no stimulants were added (spontaneous); and cytokine production in such peripheral blood neutrophils which were stimulated with lipopolysaccharide (LPS). It was revealed that there was no difference between the normal subjects and the UC patients in terms of cytokine production, and particularly in terms of interleukin 6 (IL-6) production, when no stimulants were added. It was also revealed that the UC patients showed higher cytokine production levels, and particularly higher IL-6 or tumor necrosis factor α (TNF-α) production levels, upon LPS stimulation, compared with the normal subjects. Specifically, at and after 6 hours following the start of culture, the amounts of IL-6 or TNF-α produced by the neutrophils of the UC patients were higher than the amounts produced by the neutrophils of the normal subjects. 24 hours later, the amounts of cytokines produced by the neutrophils of the UC patients were significantly higher than the amounts produced in the normal subjects. Furthermore, the neutrophils of the UC patients were compared with the same of the normal subjects in terms of the mRNA expression level of Toll-like receptor 4 (TLR4), which recognizes LPS. The levels of such mRNA expression were significantly higher in the UC patients. Based on the results, the present inventors hypothesized that the neutrophils of UC patients had already been primed by bacteria such as Gram-negative bacteria.

Such characteristics of neutrophils are similar to those of neutrophils during septicemia. It is thought that neutrophils during septicemia have lowered phagocytic activity or lowered protective functions against infections, since phagocytosis leads to cell death by necrosis (Marsik C, Mayr F, Cardona F et al., Endotoxaemia Modulates Toll-like Receptors on Leucocytes in Humans, British Journal of Haematology, 2003 121: 653-656; Hayashi F, Means T. K, Luster A. D et al., Toll-like Receptors Stimulate Human Neutrophil Function, Blood 2003 102(7): 2660-2669; and Ayala A, Chung C-S, Lomas J. L, et al., Animal Model-Shock-Induced Neutrophil Mediated Priming for Acute Lung Injury in Mice, American Journal of Pathology 2002: 161(6) 2283-2294). In general, neutrophils phagocytize microorganisms, undergo apoptosis, and then are phagocytized and removed by macrophages without releasing various intracellular mediators including granulocyte elastase, resulting in disappearance of inflammation. However, neutrophils that have undergone necrosis release mediators and undergo granulation without being removed by macrophages, resulting in protracted inflammation (Matsuda T, Saito H, Fukatsu K, et al., Differences in Neutrophil Death among β-lactam Antibiotics after in vitro Killing of Bacteria, SHOCK 2002 18(1): 69-74).

Patients who are candidates for surgical operations on digestive system organs also have lowered protective functions (of neutrophils) against infections, as in the cases of neutrophils during septicemia. Hence, such patients are susceptible to SSI. SSI should be suppressed if the protective functions of neutrophils against infections can be restored to normal levels by some means. Examples of a means for restoring the protective functions of neutrophils against infections to normal levels include a method using an extracorporeal circulatory leukocyte removal filter, a centrifugation method, batch-type leukocyte removal, and a method using a pharmaceutical such as a granulocyte colony stimulating factor (G-CSF).

Based on the above results, it is inferred that: (1) neutrophils of patients who are candidates for operations on digestive system organs increase and have lowered protective functions against infections, as observed during septicemia; (2) removal of the neutrophils by leukocyte apheresis from peripheral blood results in recruitment of new neutrophils from the bone marrow and normalization of neutrophil functions such as cytokine production capability; and then (3) the protective functions of neutrophils against infections are restored so as to suppress SSI.

Based on such action mechanism for suppressing SSI, the present inventors have focused particularly on the timing for removing leukocytes in order to improve conventional ELAD protocols. As described in Example 6, it was revealed that the numbers of neutrophils and IL-6 and IL-1ra levels started to increase during operation and reached maximum levels within 2 hours after operation. This may be due to the increased number of neutrophils because of operative stresses and the thus enhanced cytokine production. Comprehensive evaluation of these results leads to the conclusion that LCAP is preferably initiated within 2 hours after operation for suppressing leukocytes and cytokines to be produced by them, so as to control SSI. Furthermore, results that support this conclusion could be obtained as a result of examination of the cytokine production levels after exposure to LPS as described in Example 7. Specifically, the cytokine production levels (after exposure to LPS) at 3 hours and the same at 6 hours after the start of culture were the same, but the cytokine production levels increased within 6 and 24 hours after the start of culture. Accordingly, it was concluded that it is desirable to perform postoperative ELAD within at least 6 hours after operation.

Specifically, the present inventors have concluded that the most effective measure for suppressing SSI onset is to restore the protective functions of neutrophils against infections immediately after operation. Thus, the present inventors have completed the present invention. Therapeutic results can be surprisingly improved by the use of the present invention. As described in the Examples, conventional ELAD protocols resulted in an SSI incidence rate of approximately 33% and could not be said to be sufficient compared with therapeutic results achieved without ELAD protocols (SSI incidence rate of approximately 52%). However, the use of the method of the present invention resulted in significant improvement in therapeutic results, such that, surprisingly, no SSI developed (Shigeyuki Yoshiyama, Seiyu Mild, Yuki Koike, et al., Prospective Trial concerning Perioperative Leukocyte Apheresis for Improvement in Postoperative Morbidity of Ulcerative Colitis, Japanese Society of Gastroenterological Surgery, The $59^{th}$ Annual Meeting of the Japanese Society of Gastroenterological Surgery, vol. 37, no. 7, 2004).

As described above, according to the present invention, it has become possible to more efficiently suppress SSI that take place after surgical operation, and particularly, after operation on the digestive system, through the removal of leukocytes from the peripheral blood of patients during or after operation, when operative stress reactions in vivo reach the maximum levels. Furthermore, according to the present invention, a chemotherapeutic drug for treating or preventing SSI, which is used in combination with such method, is also provided.

Specifically, the following (1) to (44) are provided according to the present invention.

(1) A method for suppressing a surgical site infection associated with surgical operation on a digestive system organ, which comprises the steps of:

(a) administering a chemotherapeutic drug for treating and/or preventing a surgical site infection; and (b) collecting blood from a surgical subject and removing leukocytes that comprise neutrophils from the blood during or within 24 hours after surgical operation, and then returning the blood from which the leukocytes have been removed to the surgical subject.

(2) The method for suppressing a surgical site infection according to (1), wherein the number of leukocytes that comprise neutrophils and are removed is $6 \times 10^7$ or more and $1 \times 10^9$ or less per kg of the body weight of a surgical subject.

(3) The method for suppressing a surgical site infection according to (1), wherein the digestive system organ is selected from among the esophagus, stomach, small intestine, large intestine, rectum, colon, appendix, liver, pancreas, and gallbladder.

(4) The method for suppressing a surgical site infection according to (1), wherein the surgical subject is a patient who has inflammatory bowel disease or cancer of a digestive system organ.
(5) The method for suppressing a surgical site infection according to (1), wherein leukocytes comprising neutrophils are removed during or within 2 hours after surgical operation.
(6) The method for suppressing a surgical site infection according to (1), wherein the chemotherapeutic drug for treating and/or preventing a surgical site infection is selected from among penicillin antibiotics, cephem antibiotics, macrolide antibiotics, tetracycline antibiotics, fosfomycin antibiotics, aminoglycoside antibiotics, and new quinolone antibiotics.
(7) The method for suppressing a surgical site infection according to (1), wherein leukocytes comprising neutrophils are removed using either a method that comprises removing leukocytes comprising neutrophils with the use of a specific gravity difference between erythrocytes and leukocytes by means of a centrifuge or a method that comprises removing leukocytes comprising neutrophils with the use of a carrier having affinity for leukocytes.
(8) The method for suppressing a surgical site infection according to (7), wherein the carrier having affinity for leukocytes is selected from among a cellulose derivative containing cellulose acetate, polyester, polyolefin, poly(vinylidene fluoride), polyamide, polyimide, polyurethane, polysulfone, and polyacrylonitrile.
(9) The method for suppressing a surgical site infection according to (1), wherein the blood flow rate in step (b) ranges from 20 mL/minute to 100 mL/minute.
(10) The method for suppressing a surgical site infection according to (1), wherein the amount of blood that is collected from a surgical subject in step (b) ranges from 0.9 L to 3 L.
(11) The method for suppressing a surgical site infection according to (1), wherein nafamostat mesilate is used as an anticoagulant in step (b).
(12) A blood processing method for a surgical subject, wherein leukocytes comprising neutrophils are removed from the blood of a surgical subject during or within 24 hours after surgical operation on a digestive system organ.
(13) The blood processing method for a surgical subject according to (12), wherein the number of leukocytes that comprise neutrophils and are removed is $6 \times 10^7$ or more and $1 \times 10^9$ or less per kg of the body weight of the surgical subject.
(14) The blood processing method for a surgical subject according to (12), wherein the digestive system organ is selected from among the esophagus, stomach, small intestine, large intestine, rectum, colon, appendix, liver, pancreas, and gallbladder.
(15) The blood processing method for a surgical subject according to (12), wherein the surgical subject is a patient who has inflammatory bowel disease or cancer of a digestive system organ.
(16) The blood processing method for a surgical subject according to (12), wherein leukocytes comprising neutrophils are removed during or within 2 hours after surgical operation.
(17) The blood processing method for a surgical subject according to (12), wherein leukocytes comprising neutrophils are removed using either a method that comprises removing leukocytes comprising neutrophils with the use of a specific gravity difference between erythrocytes and leukocytes by means of centrifuge or a method that comprises removing leukocytes comprising neutrophils with the use of a carrier having affinity for leukocytes.
(18) The blood processing method for a surgical subject according to (12), wherein the carrier having affinity for leukocytes is selected from among a cellulose derivative containing cellulose acetate, polyester, polyolefin, poly(vinylidene fluoride), polyamide, polyimide, polyurethane, polysulfone, and polyacrylonitrile.
(19) A chemotherapeutic drug for treating and/or preventing a surgical site infection, which is used in combination with the blood processing method according to (12).
(20) The chemotherapeutic drug for treating and/or preventing a surgical site infection according to (19), which is selected from among penicillin antibiotics, cephem antibiotics, macrolide antibiotics, tetracycline antibiotics, fosfomycin antibiotics, aminoglycoside antibiotics, and new quinolone antibiotics.
(21) A column for blood circulation which is filled with a carrier having affinity for leukocytes comprising neutrophils, which is used for suppressing a surgical site infection during or within 24 hours after surgical operation on a digestive system organ.
(22) The column according to (21), wherein the carrier having affinity for leukocytes comprising neutrophils is selected from among a cellulose derivative containing cellulose acetate, polyester, polyolefin, poly(vinylidene fluoride), polyamide, polyimide, polyurethane, polysulfone, and polyacrylonitrile.
(23) The column according to (21), wherein the digestive system organ is selected from among the esophagus, stomach, small intestine, large intestine, rectum, colon, appendix, liver, pancreas, and gallbladder.
(24) The column according to (21), wherein the surgical subject is a patient who has inflammatory bowel disease including ulcerative colitis or cancer of a digestive system organ.
(25) The column according to (21), wherein leukocytes comprising neutrophils are removed during or within 2 hours after surgical operation.
(26) A column for blood circulation which is with a carrier having affinity for leukocytes comprising neutrophils, which is used for suppressing a surgical site infection by lowering a granulocyte elastase level in the blood of a surgical subject during or within 24 hours after surgical operation on a digestive system organ.
(27) The column according to (26), wherein the carrier having affinity for leukocytes comprising neutrophils is selected from among a cellulose derivative containing cellulose acetate, polyester, polyolefin, poly(vinylidene fluoride), polyamide, polyimide, polyurethane, polysulfone, and polyacrylonitrile.
(28) The column according to (26), wherein the digestive system organ is selected from among the esophagus, stomach, small intestine, large intestine, rectum, colon, appendix, liver, pancreas, and gallbladder.
(29) The column according to (26), wherein the surgical subject is a patient who has inflammatory bowel disease including ulcerative colitis or cancer of a digestive system organ.
(30) The column according to (26), wherein leukocytes comprising neutrophils are removed during or within 2 hours after surgical operation.
(31) A method for suppressing a surgical site infection, which comprises causing the blood of a surgical subject to come into contact with a carrier having affinity for leukocytes comprising neutrophils during or within 24 hours after surgical operation on a digestive system organ, so as to lower the blood granulocyte elastase level.
(32) The method for suppressing a surgical site infection according to (31), wherein the digestive system organ is selected from among the esophagus, stomach, small intestine, large intestine, rectum, colon, appendix, liver, pancreas, and gallbladder.

(33) The method for suppressing a surgical site infection according to (31), wherein the surgical subject is a patient who has an inflammatory bowel disease including ulcerative colitis or cancer of a digestive system organ.

(34) The method for suppressing a surgical site infection according to (31), wherein leukocytes comprising neutrophils are removed during or within 2 hours after surgical operation.

(35) The method for suppressing a surgical site infection according to (31), which is used in combination with a chemotherapeutic drug for treating and/or preventing a surgical site infection.

(36) The method for suppressing a surgical site infection according to (35), wherein the chemotherapeutic drug for treating and/or preventing a surgical site infection is selected from among penicillin antibiotics, cephem antibiotics, macrolide antibiotics, tetracycline antibiotics, fosfomycin antibiotics, aminoglycoside antibiotics, and new quinolone antibiotics.

(37) A blood processing method, which comprises causing the blood of a surgical patient to come into contact with a carrier having affinity for leukocytes comprising neutrophils during or within 24 hours after operation so as to lower the blood granulocyte elastase level, in order to suppress a surgical site infection that takes place after surgical operation on a digestive system organ.

(38) The blood processing method according to (37), wherein the digestive system organ is selected from among the esophagus, stomach, small intestine, large intestine, rectum, colon, appendix, liver, pancreas, and gallbladder.

(39) The blood processing method according to (37), wherein the surgical subject is a patient who has inflammatory bowel disease including ulcerative colitis or cancer of a digestive system organ.

(40) The blood processing method according to (37), wherein leukocytes comprising neutrophils are removed during or within 2 hours after surgical operation.

(41) The blood processing method according to (37), which is used in combination with a chemotherapeutic drug for treating and/or preventing a surgical site infection.

(42) The blood processing method according to (41), wherein the chemotherapeutic drug for treating and/or preventing a surgical site infection is selected from among penicillin antibiotics, cephem antibiotics, macrolide antibiotics, tetracycline antibiotics, fosfomycin antibiotics, aminoglycoside antibiotics, and new quinolone antibiotics.

(43) A chemotherapeutic drug for treating and/or preventing a surgical site infection, which is used in combination with the method for suppressing a surgical site infection according to any one of (31) to (34) or the blood processing method according to any one of (37) to (40).

(44) The chemotherapeutic drug according to (43), wherein the chemotherapeutic drug for treating and/or preventing a surgical site infection is selected from among penicillin antibiotics, cephem antibiotics, macrolide antibiotics, tetracycline antibiotics, fosfomycin antibiotics, aminoglycoside antibiotics, and new quinolone antibiotics.

MOST PREFERRED EMBODIMENTS OF THE INVENTION

Hereafter, the present invention is described in detail.

The present invention relates to a method for suppressing a surgical site infection (SSI) associated with surgical operation on a digestive system organ by the removal of leukocytes from the peripheral blood of a surgical subject during or after surgical operation.

A "digestive system organ" in the present invention is not particularly limited. Examples of such digestive system organ include the esophagus, stomach, small intestine, large intestine, rectum, colon, appendix, liver, pancreas, and gallbladder. Examples of a surgical subject who is a target of the method of the present invention include patients who have inflammatory bowel disease or cancer of digestive system organs. Examples of "cancer of a digestive system organ" include esophageal cancer, gastric cancer, small intestine cancer, large bowel cancer, colon cancer, rectal cancer, liver cancer, pancreatic cancer, gallbladder cancer, and biliary tract cancer.

There are 5 types of leukocytes; neutrophils, eosinophils, basophils, monocytes, and lymphocytes. Neutrophils, eosinophils, and basophils are together referred to as granulocytes. "Leukocytes comprising neutrophils" in the present invention means leukocytes at least comprising neutrophils; that is, comprising granulocytes, monocytes, and lymphocytes in addition to neutrophils. Such leukocytes may be any leukocytes that comprise neutrophils and may be leukocytes that do not comprise granulocytes, monocytes, or lymphocytes. The number of leukocytes in blood and the fractional rate of each blood component slightly differ between children and elderly people, but do not differ due to sexuality and are almost constant. For example, in an adult, the number of leukocytes in blood is approximately 6700 cells/μl and the average fractional rates are 55.3% (neutrophils), 3.5% (eosinophils), 0.5% (basophils), 5.0% (monocytes), and 36.6% (lymphocytes). Furthermore, among leukocytes, granulocytes are present in the largest number and they contain elastase in large amounts. It is thought that granulocyte elastase is released in response to stimulations or damages against granulocytes by phagocytes or inflammation or stimulations due to invasion of bacteria or foreign proteins into a body, so as to cause tissue disruption (inflammatory responses). Granulocyte elastase is neutral serine protease and has low substrate specificity, and it is the means by which almost all constitutive proteins of a living body, such as elastin, collagen, proteoglycan, and fibronectin, can be easily lysed. Moreover, granulocyte elastase has a molecular weight of 29500 and immediately binds to an inhibitor such as α1-plasmin inhibitor or α2-macroglobulin in plasma and body tissues, so as to be inactivated. Elastase concentration in plasma is generally approximately one-several hundreds of the concentration in granulocytes. Furthermore, granulocyte elastase differs from elastase derived from the pancreas. An antibody against granulocyte elastase never cross-reacts with such elastase derived from the pancreas. The activity of granulocyte elastase may be determined by separating plasma from blood and then determining elastase activity in the plasma by a method such as latex aggregation nephelometry (Mitsubishi Kagaku Bio-Chemical Laboratories, Inc.) or granulocyte elastase EIA (Sanwa Kagaku Kenkyusho Co., Ltd.). In an example of the present invention, a surgical site infection can be suppressed by causing the blood of a surgical subject to come into contact with a carrier having affinity for leukocytes comprising neutrophils during or within 24 hours after surgical operation on a digestive system organ, so as to lower the blood granulocyte elastase level.

There are two types of methods for removing leukocytes from peripheral blood: a method that involves separating leukocytes from peripheral blood using a centrifuge by the use de of a specific gravity difference between erythrocytes and leukocytes; and a method that involves removing leukocytes using a column for blood circulation which is filled with a carrier having affinity for leukocytes. Either of the above methods can be used in the present invention.

A centrifugation method begins from a so-called "draw" step of collecting whole blood from a donor in a centrifuge and then separating the whole blood into high density, intermediate density, and low density components. After sampling of a required blood component, the centrifugation method finishes at the so-called "return" step of returning the blood components remaining in a disposable system to the donor. Currently, one of the mainstream methods is an intermittent blood flow method. During aphersis, collection of a fluid from a donor into an apparatus and return of the fluid from the apparatus to the donor are performed through a single pathway, such as a blood collection needle. Conventional centrifugation methods have been improved by various techniques. Examples of such improved steps are: a so-called "dwell" step of sampling low density components outside the centrifuge and then returning the components to the centrifuge and recirculating them for a short time period; and a so-called "surge" step of recirculating low density components at a surge flow rate; that is, a flow rate that increases with time within a centrifuge, allowing blood platelets and the like to be preferentially displaced from the intermediate density components. Generally, this centrifugation method is currently performed by repeating a cycle comprised of these steps several times, so as to collect predetermined blood components. Moreover, the draw step has also been improved. Specifically, it has been proposed that the flow rate of plasma that passes through a centrifuge during the draw step or the rotational frequency of a centrifuge be selected depending on a donor, and then the process volume of whole blood per cycle would be controlled to achieve optimum conditions for each donor. One such cycle requires about 15 minutes on average and is repeated multiple times. A specific example of an apparatus that can be used for an extracorporeal-blood-circulation-type centrifugation method is a CCS haemonetics component collection system (Component Collection System, Haemonetics Co., Braintree, Mass., U.S.), which is an apparatus for collecting blood components. With this system, a citric acid dextrose (ACD, Acid Citrate Dextrose) solution or the like is used as an anticoagulant, blood access is achieved via a single indwelling catheter in cubital vein or the like, and then blood removal and blood return can be performed through such route. In addition, when such extracorporeal-blood-circulation-type centrifuge cannot be used, the use of a batch-type centrifugation method is also possible. Specifically, blood removal and blood return can also be achieved by collecting blood from a patient, separating and removing leukocyte components by centrifugation, and then returning the blood from which leukocytes have been removed to the patient.

Leukocytes can also be removed using a column for blood circulation, which is filled with a carrier having affinity for leukocytes. Examples of such carrier having affinity for leukocytes, which is used herein, include various carriers that have been used for leukocyte apheresis. Specific examples of such carrier include: cellulose, a cellulose derivative containing cellulose acetate, and polyester such as polyethylene terephthalate and polybutyrene terephthalate; polyolefin such as polyethylene and polypropylene; and polymer materials such as poly(vinylidene fluoride), polyamide, polyimide, polyurethane, polysulfone, and polyacrylonitrile. Of these, polyester nonwoven fabric, cellulose beads, and the like are suitably used. Here, "having affinity for leukocytes" means to have a single type of affinity for all leukocytes or means to have different types of affinity for granulocytes, monocytes, lymphocytes, and the like which are of leukocyte subclasses. The phrase "having affinity for leukocytes" means to have affinity at least for neutrophils. In addition, "having affinity for leukocytes" means to be able to adsorb leukocytes.

To improve the capability of a carrier to remove leukocytes, to impart selective adhesiveness to leukocyte subclasses such as granulocytes, or to prevent other blood components such as blood platelets from adhering, a carrier may be subjected to surface treatment by a method such as coating or radiation graft or subjected to fixation with a ligand such as an antibody.

Such carriers may be in the form of fibers (nonwoven fabrics and fabric cloth), porous bodies, particles (granules or beads), films, flat membranes, or hollow fibers. In the present invention, contact with blood is preferably performed via a column preferably filled with such carrier. Specifically, a removal column that is preferably used herein is composed of a blood inlet, a leukocyte removal part provided with a carrier (e.g., nonwoven fabrics or beads) having affinity for leukocytes, and a blood outlet.

Specific examples of such column include columns that have already been clinically used for various types of leukocyte apheresis, such as a leukocyte removal column that is marketed under the commercial name of "CELLSORBA" (trademark) (Asahi Kasei Medical Co., Ltd) and a granulocyte removal column marketed in the commercial name of "ADACOLUMN" (trademark) (JIMRO Co., Ltd).

The scope of the present invention also encompasses a column for blood circulation, which is filled with a carrier having affinity for leukocytes and is used during or within 24 hours after surgical operation on a digestive system organ for suppressing a surgical site infection.

According to the present invention, the blood of a surgical patient who has been operated for ulcerative colitis is caused to extracorporeally circulate using the above column, for example, so as to remove peripheral blood leukocytes. Thus, it becomes possible to prevent SSI onset. A carrier having affinity for leukocytes may be used not only for an extracorporeal-circulatory-type method, but also for a batch-type method. Specifically, prevention of SSI onset can also be achieved by collecting the blood of a patient once, separating and removing leukocyte components using a carrier having affinity for leukocytes, and then returning the blood from which leukocytes have been removed to the patient.

In the fields concerning pharmaceutical formulations for transfusion of a relatively small amount of blood, for the purpose of removing leukocytes from such a pharmaceutical formulation, a leukocyte removal apparatus for transfusion provided with nonwoven fabric layers laminated together on a flat plate has been developed and broadly employed for practical use. In such leukocyte removal apparatus for transfusion, a pre-filter is used on the upstream side of a main filter for the purpose of removing blood microaggregates. Attempts that have been made concerning such pre-filter are: designing the average fiber diameter to be sequentially or continuously smaller from the filter inlet side to the filter outlet side; and realizing a higher filter porosity to prevent clogging so as to prolong the filter lifetime and to shorten treatment time. A filter that is used for such application can also be used for application in the present invention. Examples of such transfusion filter include "SEPACELL" (trademark) (Asahi Kasei Medical CO., LTD), "IMUGARD" (trademark) III (Terumo Corporation), and "PURECELL" (trademark) (Pall Corporation).

As an extracorporeal circulatory system, a general extracorporeal circulatory system that is used for blood purification therapy or the like can be employed. Specifically, such extracorporeal circulatory system is composed of at least a blood collection needle, a means for collecting blood, such as a catheter, a means for sending blood, such as a blood pump, a leukocyte removal column, and a means for returning blood (examples of which are the same for those of the means for collecting blood), and such components are connected in this order in a liquid-tight manner via tubes or the like for causing blood to be treated to flow. Such extracorporeal circulatory system may also be provided with a means for adding a drug, an anticoagulant, or the like to blood for anticoagulation of blood. Examples of an anticoagulant that can be used in the extracorporeal circulatory system include nafamostat mesilate and the like. Furthermore, the system may also be provided with a means for measuring blood flow rates, pressure, or the like.

Conditions for blood circulation treatment cannot be simply limited and differ depending on subject, pathological conditions of the subject, and the like. In general, blood circulation can be performed under conditions of a blood flow rate between 20 mL/minute and 100 mL/minute and with about 30 minutes to 2 hours of blood circulation. The amount of blood to be collected from a subject preferably ranges from 0.9 L to 3 L. In addition, blood circulation treatment conditions can be varied by changing the amount of carrier to be used or by changing property of adsorption. Blood can be removed from a patient via either vein or artery.

Leukocyte removal is initiated during or after surgical operation, when an in vivo operative stress reaction reaches the maximum level. In the present invention, "during surgical operation" means a condition in which an affected site is incised, more preferably refers to the latter half of operation, and further preferably refers to a time after completion of major surgical treatment but before suturing of the skin at the incised site. Furthermore, in the present invention, "postoperative or after operation" means a time after completion of suturing of the skin at the incised site and after termination of surgical invasion of a patient. The present invention is performed within 72 hours, preferably within 48 hours, and further preferably within 24 hours after operation. Moreover, the amounts of IL-6 and TNF-α produced by neutrophils of a UC patient start to increase at 6 hours after LPS exposure. Thus, postoperative leukocyte apheresis is even further preferably performed within 6 hours after operation. Furthermore, postoperative leukocyte apheresis is most preferably performed within 2 hours after operation in view of the number of neutrophils and cytokine levels determined for a UC patient after operation. The number of leukocyte removal to be performed may be one, but leukocyte removal can also be performed at several separate times.

As shown in the following Example 2, in the case of an LCAP group (subjected to LCAP), a total of 1500 mL of blood was processed at a blood flow rate of 50 mL/minute×30 minutes and sufficient clinical effects were confirmed. The number of these leukocytes removed in this case was approximately $5 \times 10^9$ or approximately $1 \times 10^8$ per kg body weight. Furthermore, as demonstrated in an animal model experiment in Example 4, SSI onset can be suppressed by removing at least $6 \times 10^7$ leukocytes per kg body weight. Such effect of suppressing SSI onset is mainly due to neutrophil removal and the resulting recovery of neutrophils' functions to prevent infections. Hence, successful removal of at least $6 \times 10^7$ neutrophils per kg body weight may result in a sufficient clinical effect. Such processing clinically corresponds to processing of a total of 900 mL of blood by GCAP (at a blood flow rate of 30 mL/minute×30 minutes) (Example 3). With this processing, overall, $3 \times 10^9$ granulocytes are removed. Moreover, a method employed for leukocyte removal may be either a centrifugation method or a method using a leukocyte removal filter (Example 4).

Hence, the number of leukocytes that should be removed to obtain the effect of the present invention is $3 \times 10^9$ or more and preferably $5 \times 10^9$ or more, or $6 \times 10^7$ or more, and more preferably $1 \times 10^8$ or more per kg body weight. In the meantime, the maximum number of leukocytes to be removed is not particularly limited. Actually, it is not practical to remove more leukocytes than exist in total in peripheral blood, because this may cause side effects or the like. Specifically, it is not practical to remove approximately $1 \times 10^9$ or more leukocytes per kg body weight.

According to the present invention, SSI can be suppressed by a combined use of such leukocyte removal and a chemotherapeutic drug that is generally used for the purpose of preventing infectious disease. The scope of the present invention also encompasses such chemotherapeutic drug for treating and/or preventing surgical site infections, which is used in combination with the method for suppressing surgical site infections or the blood processing method according to the present invention.

In general, "chemotherapy" means to treat disease caused by a pathogenic parasite (e.g., bacteria, viruses, and fungi) by administering a chemical substance that kills or inhibits the growth of the pathogenic parasite. A drug used for such chemotherapy is referred to as a chemotherapeutic drug. In the present invention, examples of a chemotherapeutic drug include metabolites produced by various microorganisms, which suppress the growth of other bacteria or microorganisms, such as antibiotics (e.g., penicillin). Specific examples of such chemotherapeutic drug include penicillin antibiotics, cephem antibiotics, macrolide antibiotics, tetracycline antibiotics, fosfomycin antibiotics, aminoglycoside antibiotics, and new quinolone antibiotics. As described above, for operations on the lower digestive tract, or the like, drugs having wide-ranging antibacterial spectra, such as second- (and following)-generation cephem, carbapenem antibiotics, and new quinolone antibiotics are used. Examples of second-generation cephem antibiotics include cefotiam dihydrochloride (CTM), cefmetazole sodium (CMZ), and cefsulodin sodium (CFS). Examples of third-generation cephem antibiotics include cefotaxime sodium (CTX), ceftizoxime sodium (CZX), cefoperazone sodium (CPZ), cefmenoxime hemihydrochloride (CMX), and latamoxef sodium (LMOX). Furthermore, examples of third (and following)-generation cephem antibiotics include cefminox sodium (CMNX), ceftriaxone (CTRX), cefbuperazone sodium (CBPZ), cefpimizole sodium (CPIZ), cefuzonam sodium (CZON), ceftazidime (CAZ), and cefoperazone/sulbactam (CPZ/SBT). Furthermore, examples of carbapenem antibiotics include imipenem/cilastatin sodium (IPM/CS) and meropenem trihydrate (MEPM). Furthermore, examples of new quinolone antibiotics include enrofloxacin (ERFX), ofloxacin (OFLX), and ciprofloxacin (CPFX).

Regarding the time for initiating the administration of a chemotherapeutic drug, it is ideal to initiate the administration through intravenous drip infusion at 1 hour before the time at which the operative field becomes contaminated at the highest level; that is, the time at which the gastrointestinal tract is opened, so that the concentration of the chemotherapeutic drug in the blood should be highest at such time. Furthermore, in long operation (of approximately more than 3 hours which is double the blood half-life), the drug is additionally administered during the operation. However, a chemotherapeutic drug may also be administered after operation, depending on the circumstances.

In the present invention, the step of administering a chemotherapeutic drug and the step of removing leukocytes may be performed in any order or may be performed simultaneously. A chemotherapeutic drug may be administered once or several separate times. The step of removing leukocytes may also be performed once or several separate times.

EXAMPLES

The present invention is hereafter described in greater detail with reference to the following examples, although the present invention is not limited thereto.

Example 1

Examination was performed on 75 ulcerative colitis (UC) patients who had surgery during December 2000 to May 2004 at the hospital to which the present inventors belong.

Non-ELAD (leukocyte apheresis) group (not subjected to ELAD): 54 cases

ELAD (leukocyte apheresis) group (subjected to ELAD): 21 cases (the therapy employed herein is as described below)
(1) Preoperative leukocyte apheresis (LCAP) group (subjected to LCAP before operation): 4 cases
(2) Preoperative granulocyte apheresis (GCAP) group (subjected to GCAP before operation): 8 cases
(3) Postoperative (immediately after operation) leukocyte apheresis group (subjected to LCAP immediately after operation; that is, subjected to the method of the present invention): 9 cases that consisted of 7 cases of postoperative (immediately after operation) granulocyte apheresis (GCAP) and 2 cases of postoperative (immediately after operation) leukocyte apheresis (LCAP).

Specifically, blood processing according to the method of the present invention was performed as follows. In the case of the groups subjected to GCAP, 1800 mL of blood was processed in total at a blood flow rate of 30 mL/minute×1 hour; that is, 35% to 70% of granulocytes in blood that had flowed into a column and 35% to 69% of monocytes in the same blood were removed. In contrast, in the case of the groups subjected to LCAP, 3000 mL of blood was processed in total at a blood flow rate of 50 mL/minute×1 hour; that is, 99% of granulocytes and monocytes in reflux blood, 60% to 79% of lymphocytes, and approximately 50% of blood platelets were removed.

In addition, in terms of original non-surgical therapy, LCAP is a stronger therapy than GCAP, and the results of LCAP are somewhat superior to those of GCAP. However, in view of the facts that postoperative (immediately after operation) GCAP has sufficient clinical effects in the present invention, that LCAP has a risk of causing adsorption of blood platelets immediately after operation, and that the yields obtainable in the case of LCAP are not required by the present invention, it was concluded that approximately 30 minutes of blood circulation would be sufficient.

These patients were examined in terms of perioperative fever, heart rate, leukocytes, and CRP. Furthermore, peripheral blood was collected from some patients in the perioperative period and then IL-1 receptor antagonist (IL-1ra), IL-6, and serum IL-6 receptor (sIL-6R) levels were determined by the ELISA method, so that perioperative fluctuations were also examined.

Results:

The ELAD group and the non-ELAD group were the same in terms of age, sex, preoperative total steroid dose, operation time, and bleeding volume. In terms of fever, heart rate, and CRP, the results of the ELAD group were significantly lower than those of the non-ELAD group on and after postoperative day 3, indicating early withdrawal from SIRS in the case of the ELAD group.

The postoperative complication incidence rate was significantly lower in the ELAD group, and the surgical site infection (SSI) incidence rate was also lowered.

There were no differences in terms of IL-1ra, IL-6, and sIL-6R fluctuations.

Regarding differences among the protocols, the postoperative (immediately after operation) ELAD group of the present invention showed a significantly high IL-6 level immediately after operation, but tended to show lower levels of fever, heart rate, and CRP, compared with the preoperative LCAP group and the preoperative GCAP group.

These results are separately shown in FIGS. 3 to 7.

FIG. 3 shows fluctuations in perioperative granulocyte elastase level and particularly shows comparison among the 21 cases of the ELAD (leukocyte apheresis) group: (1) the preoperative leukocyte apheresis (LCAP) group; (2) the preoperative granulocyte apheresis (GCAP) group; and (3) the 9 cases of the postoperative (immediately after operation) ELAD group (consisting of 7 cases of the granulocyte apheresis (GCAP) group and 2 cases of the leukocyte apheresis (LCAP) group). In addition, "POD" in the figure denotes "postoperative days." Hence, "1 POD" means "postoperative day 1." The same applies in the following figures.

As revealed from the results shown in the figures, the postoperative (immediately after operation) granulocyte apheresis (GCAP) group of the present invention showed significantly suppressed increases in postoperative granulocyte elastase, compared with the preoperative LCAP group and the preoperative GCAP group.

FIG. 4 similarly shows fluctuations in the blood IL-6 level among the 21 cases of the ELAD groups, including the preoperative LCAP group, the preoperative GCAP group, and the postoperative (immediately after operation) GCAP group of the present invention. The postoperative GCAP group of the present invention showed a high IL-6 level immediately after operation, but showed no differences on 1 POD and days following 1 POD.

FIG. 5 shows fluctuations in perioperative body temperature, which provide indications for postoperative inflammatory responses, of the non-ELAD group (54 cases) and the postoperative (immediately after operation) GCAP group/LCAP group of the present invention (a total of 9 cases). As revealed from the figure, the postoperative (immediately after operation) GCAP group/LCAP group of the present invention (a total of 9 cases) showed suppressed fever, indicating that postoperative inflammation was suppressed.

FIG. 6 shows perioperative heart rate fluctuations that provide indications for postoperative inflammatory responses in the non-ELAD group (54 cases) and the postoperative (immediately after operation) GCAP group/LCAP group of the present invention (a total of 9 cases). As revealed from the figure, the postoperative (immediately after operation) GCAP group/LCAP group of the present invention showed decreases in heart rate, indicating that postoperative inflammation was suppressed.

In addition, the relationship between perioperative IL-6 levels and surgical site infections (SSI) was examined, but no significant relationship was confirmed between the two. FIG. 7 shows the relationships between postoperative (after IAA (ileoanal anastomosis)) blood IL-6 levels and surgical site infections (SSI). As revealed from the results in the figure, no differences were found in cytokine fluctuations between the group that had developed surgical site infections and the group that had not developed SSI.

As confirmed from the above results, leukocyte apheresis (ELAD) actually caused no differences among perioperative cytokine levels. Hence, it can be understood that the uniqueness of the present invention resides in its focus on granulocyte elastase and the performance of leukocyte apheresis (ELAD) during or after operation, when in vivo operative stress reactions reach the maximum level. This allows suppression of postoperative increases in granulocyte elastase level.

The above results were comprehensively evaluated. Table 1 lists the presence or the absence of (postoperative) surgical site infections (SSI) in cases in which the method of the present invention was performed (9 cases), in which conventional leukocyte apheresis was performed (12 cases), and in which leukocyte apheresis (ELAD) was not performed (54 cases). (Figures in parentheses indicate percentages.)

TABLE 1

|        | Without ELAD | Conventional ELAD | Method of the present invention | Total |
|--------|--------------|-------------------|----------------------------------|-------|
| SSI    | 28 (51.8%)   | 4 (33.3%)         | 0 (0%)                           | 32    |
| No SSI | 26 (48.2%)   | 8 (66.7%)         | 9 (100%)                         | 43    |
| Total  | 54           | 12                | 9                                | 75    |

It was revealed by the above clinical results that the use of the method of the present invention enables early withdrawal from systemic inflammatory responses after operation for ulcerative colitis and that postoperative complications were significantly suppressed.

Example 2

The following examination was performed on 5 ulcerative colitis patients who were operated from August 2004 to September 2004 at the hospital to which the present inventors belong. Colectomy was performed for the 5 ulcerative colitis patients (5 cases) under general anesthesia. Specifically, 3 out of the 5 patients (cases) were subjected to total colectomy, J ileal pouch-anal anastomosis, and then establishment of an artificial ileum-anus. The other 2 patients (cases) were operated in a manner analogous to the above operations. The following LCAP was performed at laparotomy sites during the late operative period and particularly during anastomosing of the laparatomy site. Specifically, blood was collected via the brachial artery of each patient. The blood was applied to CELLSORBA™ at a blood flow rate of 50 ml/minute, while physiologic saline containing approximately 0.1 mg/ml nafamostat mesilate as an anticoagulant was added in an amount corresponding to approximately 12% of the volume of blood that would be caused to flow per minute. The blood was then returned to the patient via the brachial vein. The volume of blood that had been processed each time was approximately 1.5 liters and the time required for this processing was approximately 30 minutes. An average of $7.5 \times 10^9$ leukocytes were removed per patient by this processing. An average of $5.4 \times 10^9$ granulocytes were removed per patient. In terms of the number of the cells per kg body weight, an average of $1.5 \times 10^8$ leukocytes per kg body weight and an average of $1.1 \times 10^8$ granulocytes per kg body weight were removed.

Furthermore, 1 g of cefmetazole sodium (CMZ) (trade name: CEFMETAZON™) was administered intravenously as an antibiotic to each of 4 patients (cases) immediately before operation, before and after noon on postoperative day 1, before and after noon on postoperative day 2, and before noon on postoperative day 3. For the 1 other patient (case), cefotiam dihydrochloride (CTM) (trade name: PANSPORIN™) was used instead of CEFMETAZON™. With this processing, no SSI onset was confirmed in any of the 5 patients (cases) over the 30 days after operation.

Example 3

The following GCAP was performed upon colectomy for UC patients. Specifically, blood was collected from the brachial artery of each patient during the late operative period and particularly during the anastomosing of the laparotomy site. The blood was applied to ADACOL-UMN™ at a blood flow rate of approximately 30 ml/minute, while heparin was administered as an anticoagulant. The blood was then returned to the patient via the brachial vein. The volume of blood that had been processed each time was approximately 0.9 liters and the time required for this processing was approximately 30 minutes. Moreover, the antibiotic was administered during operation and until postoperative day 3. SSI onset was significantly suppressed, compared with cases in this example, in which no GCAP had been performed.

Example 4

Laparotomy is performed for groups A to F each consisting of 5 rabbits (2.5 kg to 3 kg body weights). Specifically, the abdomen of each rabbit is opened at a length of 5 cm under general anesthesia using pentobarbital. Approximately 3 cm of the large intestine is deleted, followed by re-anastomosis. Ten ml of blood is collected per kg body weight via the ear vein of each rabbit during the latter half period of operation and particularly during closing of the abdomen. Immediately after closing, heparin is added to 10 U per ml. For the groups A and B, the blood is processed with a leukocyte removal filter (4 non-woven fabrics with a diameter of 4 cm are laminated together) made of polyethylene terephthalate non-woven fabric, and then leukocyte components in blood are removed. Approximately 90% of leukocytes are removed from the processed blood by this processing. The number of rabbit leukocytes is approximately $9 \times 10^6$ per ml. Thus, it can be calculated that approximately $8 \times 10^7$ leukocytes are removed per kg body weight.

For groups C and D, 10 ml of blood to which heparin has been added after collection of blood is added to a centrifuge tube and then subjected to centrifugation at 400 G for 10 minutes using a swing centrifuge. After centrifugation, rotational frequency is gradually decreased. Buffy coats (leukocyte fractions) generated between erythrocyte and plasma layers within the centrifuge tube after centrifugation are pipetted out using a micropipette, thereby removing leukocyte components. Approximately 70% of leukocytes are removed from the processed blood by this processing. Therefore, it can be calculated that $6 \times 10^7$ leukocytes are removed per kg body weight.

The processed blood is returned via the vein of each rabbit of each group from which the blood has been collected. For the groups E and F, the collected blood, to which heparin has been added, is allowed to stand for 10 minutes and then the blood is directly returned to each rabbit from which blood has been collected. After completion of the above manipulation, an antibiotic (penicillin) is subcutaneously administered at 10 KU/kg on the day of operation, on postoperative day 1, and on postoperative day 2. Follow-up is performed until postoperative week 1. Furthermore, for groups A, C, and E, the laparotomy site of each rabbit is coated with $1 \times 10^{10}$ *Escherichia coli* (*E. coli*, ATCC25922) per kg body weight before the closing of the abdomen. Each rabbit is returned to a cage after operation, followed by 1 week of observation of the surgical site and constitutional symptoms. After 1 week of observation, many deaths are observed among the rabbits of group E. Pus discharge from the surgical sites is observed among the rabbits that have survived. Among the rabbits of groups A and C, few deaths are observed and pus discharge is observed for some of the rabbits that have survived. On the other hand, among the rabbits of the groups B, D, and F that are negative control groups, almost no deaths or pus discharge are observed.

Example 5

The following examination was performed on 4 ulcerative colitis patients who were operated in March 2005 at the hospital to which the present inventors belong. Colectomy was performed for the 4 ulcerative colitis patients (4 cases) under general anesthesia. Specifically, 3 out of the 4 patients (cases) were subjected to total colectomy, J ileal pouch-anal anastomosis, and then establishment of an artificial ileumanus. The other 1 patient (case) was operated in a manner analogous to the above operation. The following LCAP was initiated within 2 hours after operation. Here, "after operation" means "after completion of skin suturing of the incision site so as to finish surgical invasion of the patients." LCAP was performed by collecting blood from each patient via the brachial vein and then applying the blood to CELLSORBA™ at a blood flow rate of 50 ml/minute while physiologic saline containing approximately 0.1 mg/ml nafamostat mesilate as an anticoagulant was added in an amount corresponding to approximately 12% of the volume of blood that would be caused to flow per minute. The blood was then returned to the patient via the brachial vein. For 3 out of the 4 cases, the volume of blood that had been processed each time was approximately 3 liters and the time required for this processing was approximately 60 minutes. For the other 1 case, the volume of the same was approximately 1.5 liters and the time required for the same was 30 minutes. Furthermore, 1 g of cefmetazole sodium (CMZ) (trade name: CEFMETAZON™) was administered intravenously as an antibiotic to all patients (all cases) immediately before operation, at 3 hours after the start of operation, during the night of the day of operation, before and after noon on postoperative day 1, before and after noon on postoperative day 2, and before and after noon on postoperative day 3. SSI evaluation was performed as defined in the "Guideline for Prevention of Surgical Site Infection (SSI) 1999" (Alicia J, Teresa C, Michele L, et al., Guideline for Prevention of Surgical Site Infection, 1999, Infection Control and Hospital Epidemiology 1999, 20 (4): 247-278) of the CDC (Centers for Disease Control and Prevention). With this treatment, no SSI onset was observed for any of the 4 patients (4 cases) over the 30 days after operation.

Example 6

Postoperative fluctuations in the number of leukocytes were examined to find the best time for performing leukocyte apheresis (LCAP). The following examination was performed for 3 ulcerative colitis (UC) patients and 2 rectal cancer patients who were operated (colectomy) from December 2004 to February 2005 at the hospital to which the present inventors belong. Table 2 lists the disease name, age, sex, operation time, anesthesia time, bleeding volume, and transfusion volume for the cases. In Table 2, RK denotes rectal cancer and UC denotes ulcerative colitis. The average operation time was 3 hours and 48 minutes. For the patients of the 5 cases listed in Table 2, blood was collected at times shown in FIG. 8 (before operation (before induction anesthesia), at 2, 4, 6, 8, 10, and 12 hours after the first collection of blood, and on postoperative day 1). The number of leukocytes, leukocyte fractions, and blood cytokine concentrations were measured. The number of leukocytes and leukocyte fractions were measured using an automatic blood cell analyzer. The concentrations in blood of cytokines including IL-1 receptor antagonist (IL-1ra) and IL-6 were measured by the ELISA method. As a result, it was revealed that the number of leukocytes started to increase during operation, significantly increased within 2 hours after induction anesthesia, and reached the maximum level at 2 hours after completion of operation. Moreover, the number of neutrophils was kept at levels that were significantly higher than the preoperative level from the start of operation to 24 hours after operation. It was revealed that the increased number of leukocytes was probably due to the effect of the increased number of neutrophils among leukocytes. It was revealed that the blood cytokine (IL-6) concentration reached the maximum level within 4 hours after induction anesthesia. It was also revealed that the blood IL-1ra concentration reached a level that was significantly higher than the preoperative level within 4 hours after induction anesthesia and reached the maximum level within 2 hours after operation.

These results are separately shown in FIGS. 9 to 14.

FIG. 9 shows fluctuation in the number of leukocytes before operation (before induction anesthesia), at 2, 4, 6, 8, 10, and 12 hours after the initial collection of blood, and on postoperative day 1. As shown in FIG. 9, the number of leukocytes started to increase during operation and reached the maximum level within 6 to 10 hours after induction anesthesia. Since the average operation time was 3 hours and 48 minutes, the number of leukocytes reached the maximum level within 2 to 6 hours after operation.

FIG. 10 shows percentage changes in the number of leukocytes, when the number that had been counted before operation was determined to be 100. The value for leukocytes significantly increased within 2 hours after the start of operation, reached the peak within 2 to 6 hours after completion of operation, and significantly increased until 24 hours after the completion of operation.

FIG. 11 shows fluctuation in the number of neutrophils. The number of neutrophils started to increase during operation and reached the maximum level within 6 to 10 hours after induction anesthesia. Since the average operation time was 3 hours and 48 minutes, the number of neutrophils reached the maximum level within 2 to 6 hours after operation.

FIG. 12 shows percentage changes in the number of neutrophils, when the number counted before operation was determined to be 100. The value for neutrophils significantly increased within 2 hours after the start of operation, reached the maximum level within 2 to 6 hours after the completion of operation, and significantly increased until 24 hours after the completion of operation.

FIG. 13 shows fluctuation in blood IL-6 level. The IL-6 level reached the maximum level within 4 hours after induction anesthesia.

FIG. 14 shows fluctuation in blood IL-1ra level. The IL-1ra level was significantly higher than the preoperative level at 4 hours after induction anesthesia and reached the maximum level within 6 hours after induction anesthesia. Since the average operation time was 3 hours and 48 minutes, the IL-1ra level reached the maximum level within 2 hours after operation.

Based on the above results, it was revealed that the number of neutrophils, the IL-6 level, and the IL-1ra level started to increase during operation and reached their maximum levels within 2 hours after operation. These results indicate that the number of neutrophils increased due to operative stresses and cytokine production was enhanced. Comprehensive evaluation of these results leads to the conclusion that LCAP is preferably initiated within 2 hours after operation, so as to suppress leukocytes and cytokines to be produced therefrom and thus to control SSI.

TABLE 2

| Case | Disease | Age | Sex | Operation time (min) | Anesthesia time (min) | Bleeding amount (g) | Blood transfusion (ml) |
|---|---|---|---|---|---|---|---|
| 1 | RK | 68 | M | 212 | 265 | 563 | None |
| 2 | RK | 74 | M | 308 | 390 | 560 | 560 (during operation) |
| 3 | UC | 22 | F | 218 | 270 | 170 | None |
| 4 | UC | 19 | M | 212 | 260 | 350 | None |
| 5 | UC | 29 | F | 191 | 310 | 67 | 720 (before operation) |

Example 7

Peripheral blood was collected from 8 UC patients before operation and 15 normal subjects, and then monocytes and neutrophils were separated from the peripheral blood of each patient (or each subject) by a standard method using FICOLL™ (trade name). The thus separated monocytes were inoculated at $5 \times 10^5$/well to a 24-well plate, followed by 3, 6, 24, and 48 hours of culture at 37° C. in media separately supplemented with control (no cytokines), IL-1β (10 ng), and LPS (100 ng). Cytokine levels in the culture supernatants were determined by the ELISA method. Furthermore, the thus separated neutrophils were inoculated at $5 \times 10^5$/well to a 24-well plate, followed by 3, 6, 24, and 48 hours of culture at 37° C. in media separately supplemented with control (no cytokines), IL-1β (10 ng), and LPS (100 ng). Cytokine levels in the culture supernatants were determined by the ELISA method. Furthermore, mRNAs were extracted from some of neutrophils before culture, and mRNA expression levels of cytokines, PMN-E (granulocyte elastase), TLR4, and the like were semiquantified by the PCR method.

FIG. 15 shows the amounts of cytokines produced and the amount of granulocyte elastase in the culture supernatant of neutrophils as measured by ELISA. In the case of monocytes, the UC patient group did not differ from the normal subject group in terms of the amounts of cytokines produced and thus the results are not shown. In FIG. 15, "UC, CO" denotes the control group of UC patients, and "CO, CO" denotes the control group of the normal subjects. In the case of neutrophils at 24 hours after stimulation of the UC patient group with LPS, the amounts of IL-6, IL-8, and TNF-α produced significantly increased, compared with those of the control. On the other hand, regarding cytokine production in the case of the neutrophils of the normal subjects, the amount of IL-6 produced did not increase even with stimulation with LPS. Furthermore, FIG. 16 shows the results of measuring the amounts of cytokines produced in the culture supernatants of neutrophils that had been cultured for 24 hours under stimulation with LPS. The amounts of inflammatory cytokines produced, such as IL-6 and TNF-α, were significantly higher in the UC patient group than those in the normal subject group. Based on the above results, it was inferred that neutrophils of the UC patients were primed by Gram-negative bacteria. Next, the mRNA expression level of TLR4 (which is an LPS receptor) in peripheral blood neutrophils was examined. The mRNA expression level was significantly higher in the UC patient group than that in the normal subject group, suggesting that one of the reasons for high sensitivity to LPS in the UC patient group was the high expression level of the LPS receptor (FIG. 17).

The above results showed that the amounts of cytokines produced (after exposure to LPS) at 3 hours after the start of culture did not differ from those at 6 hours after the same and that the amounts of cytokines produced increased within 6 to 24 hours after the start of culture. Hence, it was concluded that postoperative ELAD is preferably performed at least within 6 hours after operation.

INDUSTRIAL APPLICABILITY

The use of the method for suppressing surgical site infections and the blood processing method of the present invention enables effective suppression of SSI that have occurred at extremely high incidence rates after surgical operation on digestive system organs, particularly for inflammatory bowel diseases, and most particularly for ulcerative colitis. Furthermore, the use of the methods of the present invention enables early withdrawal from postoperative SIRS. Hence, postoperative complications can be effectively prevented. Furthermore, the combined use of the blood processing method of the present invention and a chemotherapeutic drug enables significant improvement in therapeutic or preventive effects because of synergetic effects produced by the two, the lower dose of a chemotherapeutic drug, and a shorter administration period. Thus, side effects can be prevented from occurring and the advent of drug-resistant bacteria can also be suppressed.

BRIEF DESCRIPTION OF THE DRAWINGS

FIG. 3 shows comparison among the ELAD therapy groups (subjected to ELAD therapy) including the preoperative LCAP group (subjected to LCAP before operation) and the preoperative GCAP group (subjected to GCAP before operation) and the postoperative GCAP group/LCAP group (subjected to GCAP and LCAP, respectively, immediately after operation; that is, subjected to the method of the present invention).

Figure 1:
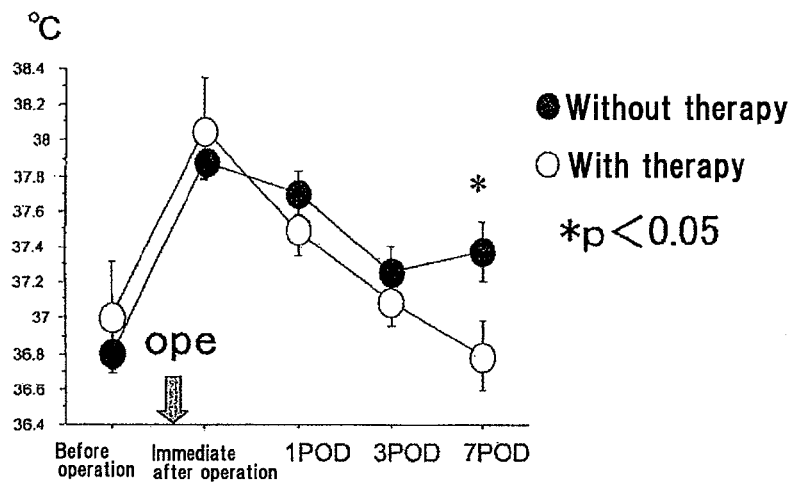
FIG. 1 shows changes in body temperature for comparison of a case with and a case without the conventional perioperative ELAD therapy in terms of postoperative inflammatory responses.
Figure 2:
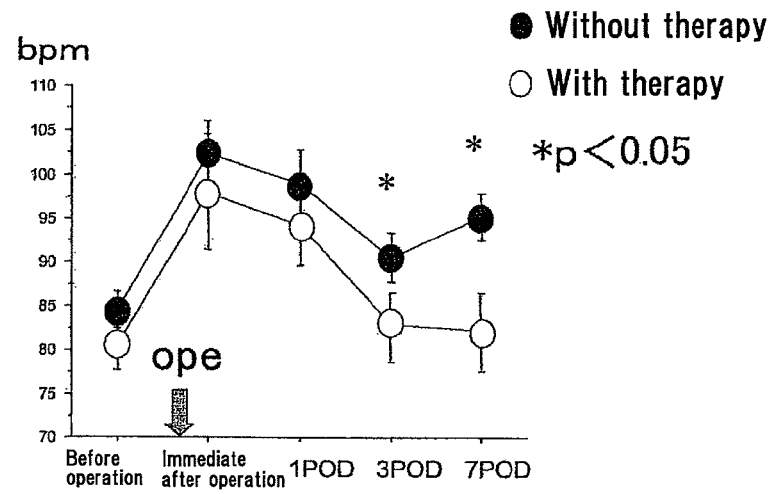
FIG. 2 shows changes in heart rate for comparison of a case with and a case without the conventional perioperative ELAD therapy in terms of postoperative inflammatory responses.
Figure 3:
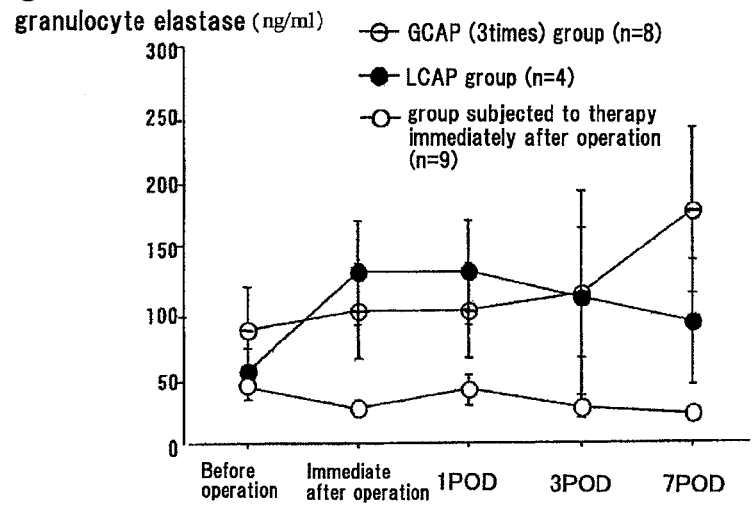
FIG. 3 shows fluctuations in the perioperative granulocyte elastase level. Specifically.
Figure 4:
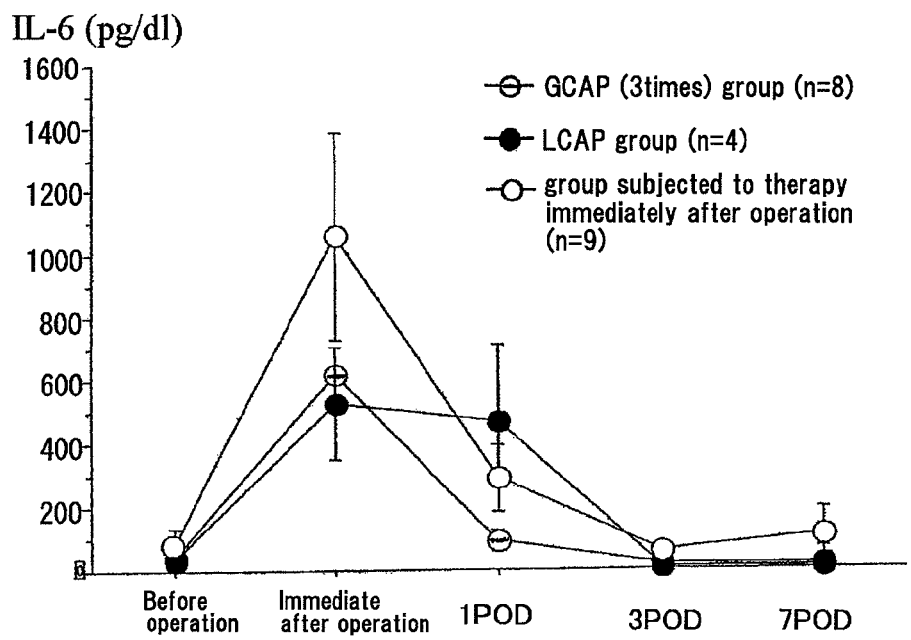
FIG. 4 shows fluctuations in blood IL-6 level among the ELAD therapy groups including the preoperative LCAP group and the preoperative GCAP group and the postoperative GCAP group/LCAP group (subjected to GCAP and LCAP, respectively, immediately after operation; that is, subjected to the method of the present invention).
Figure 5:
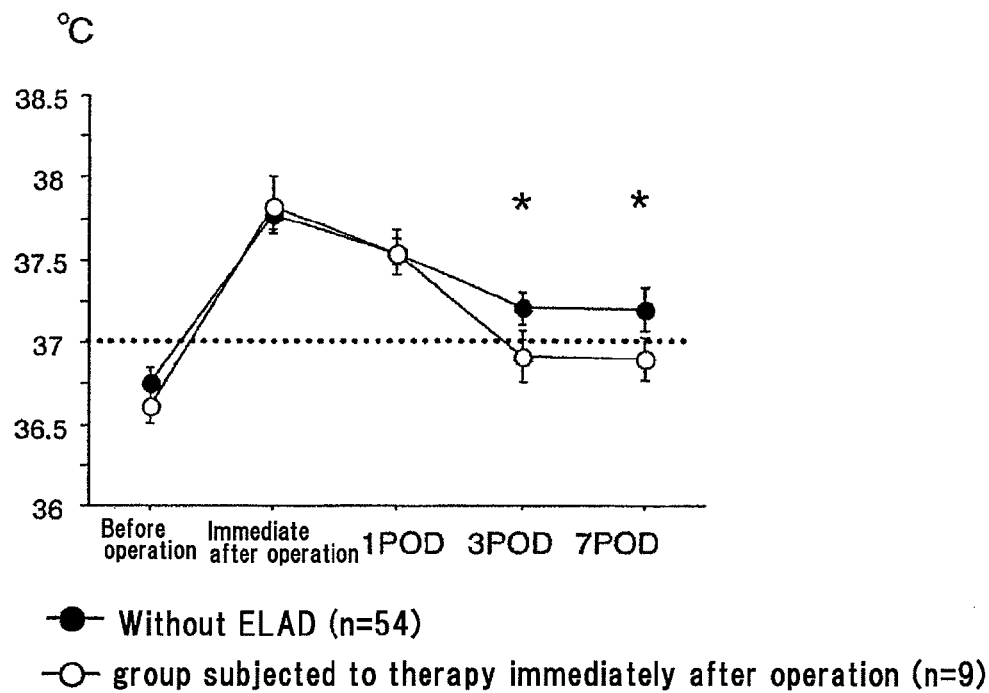
FIG. 5 shows fluctuations in perioperative body temperature, which provide indications for postoperative inflammatory responses in the non-ELAD group (not subjected to ELAD therapy) and in the postoperative GCAP group/LCAP group (subjected to GCAP and LCAP, respectively, immediately after operation; that is, subjected to the method of the present invention).
Figure 6:
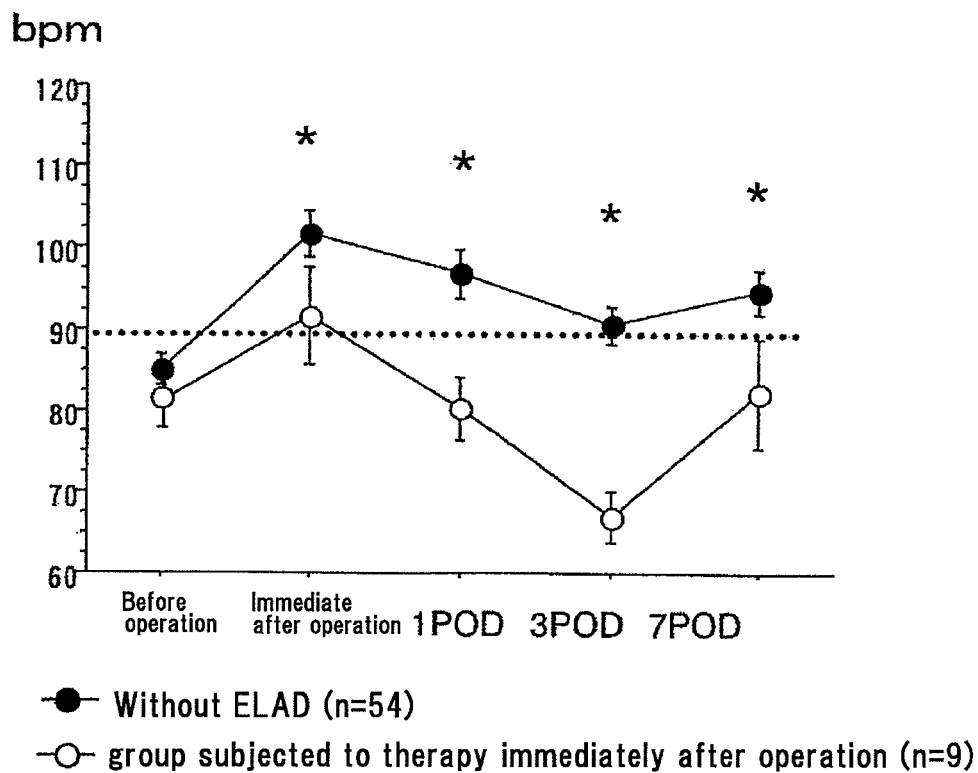
FIG. 6 shows fluctuations in perioperative heart rate, which provide indications for postoperative inflammatory responses in the non-ELAD group and the postoperative GCAP group/LCAP group (subjected to GCAP and LCAP, respectively, immediately after operation; that is, subjected to the method of the present invention).
Figure 7:
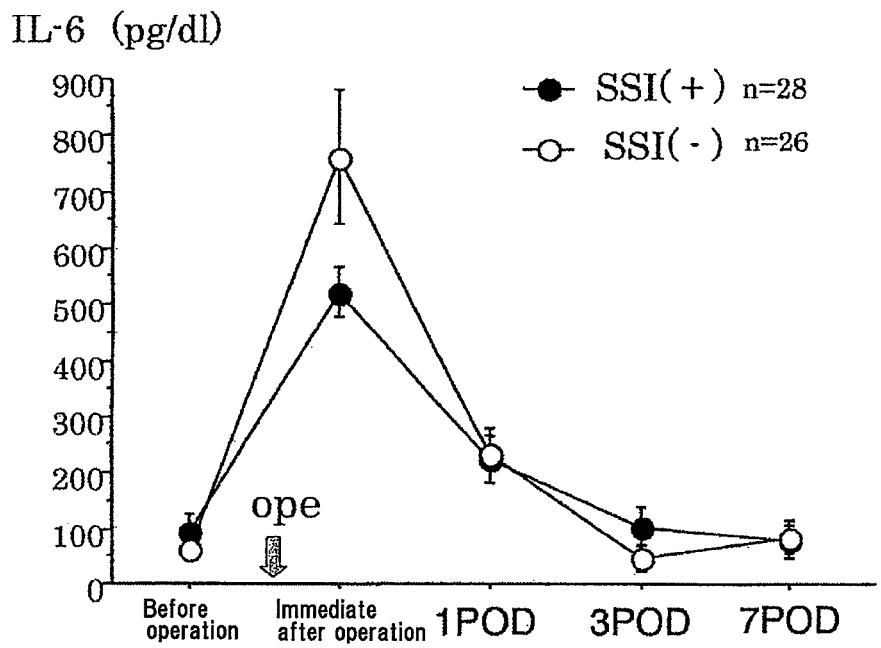
FIG. 7 shows the relationships between postoperative (after IAA (ileoanal anastomosis)) blood IL-6 levels and surgical site infections (SSIs) in the non-ELAD group.
Figure 8:
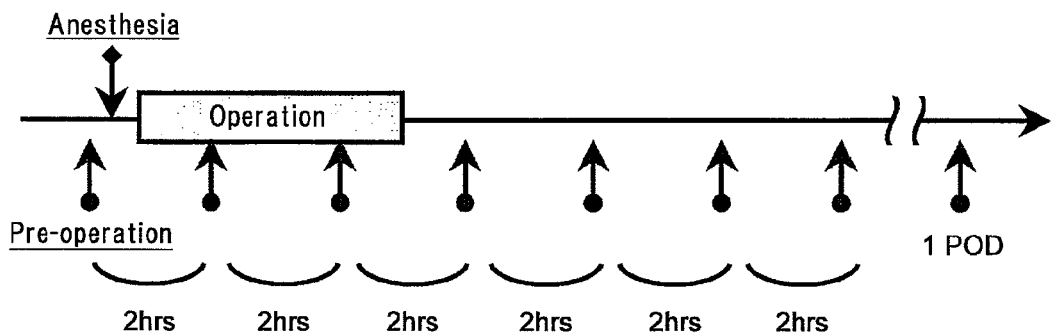
FIG. 8 is a pattern diagram showing times at which blood was collected to obtain blood cell count.
Figure 9:
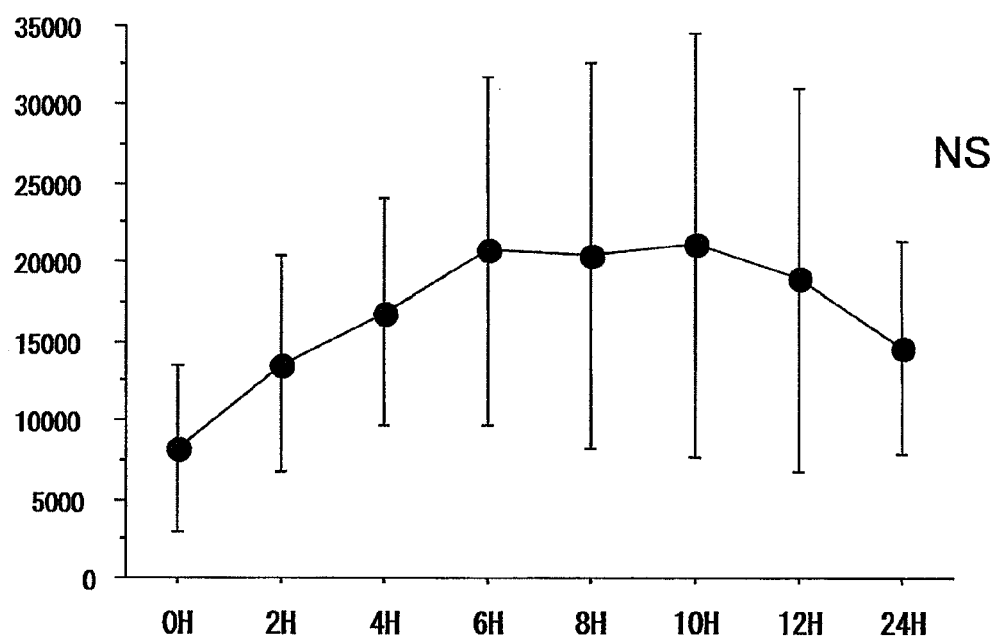
FIG. 9 shows fluctuation in the total number of leukocytes in the operation.
Figure 10:
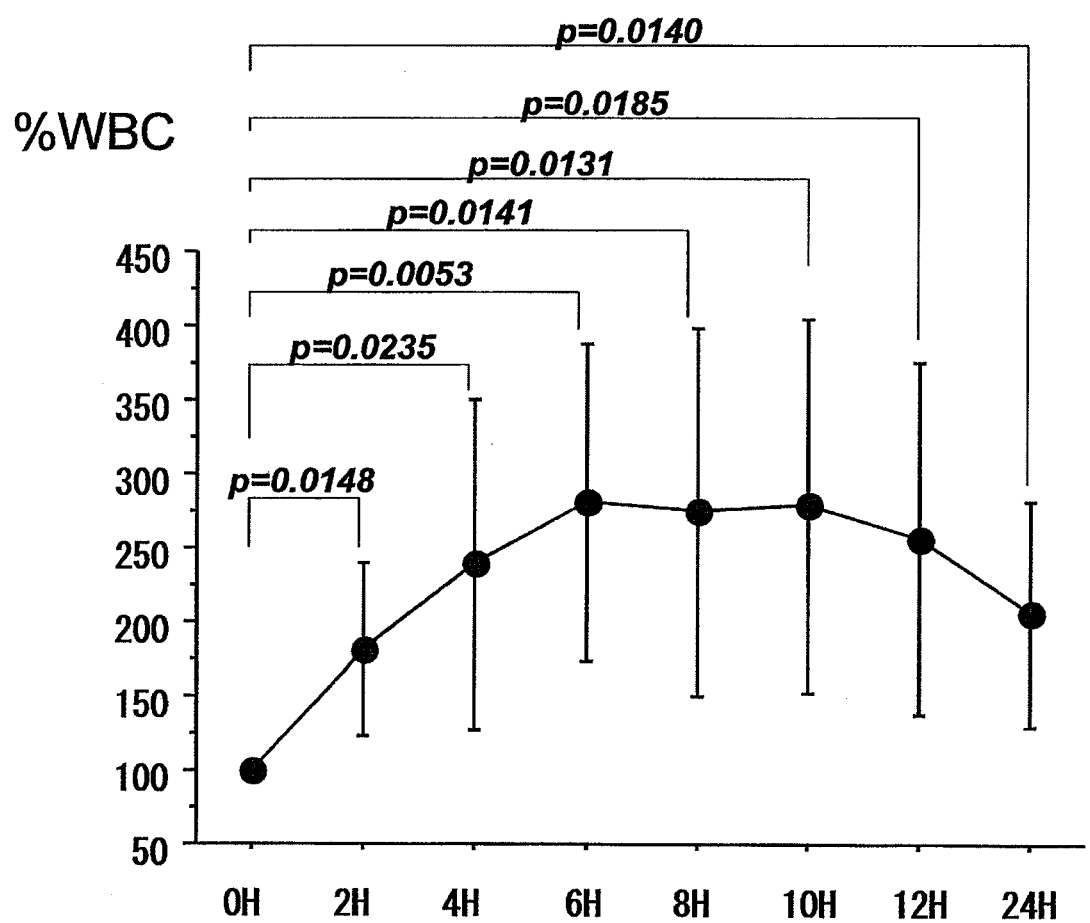
FIG. 10 shows percentage changes in the total number of leukocytes in the operation.
Figure 11:
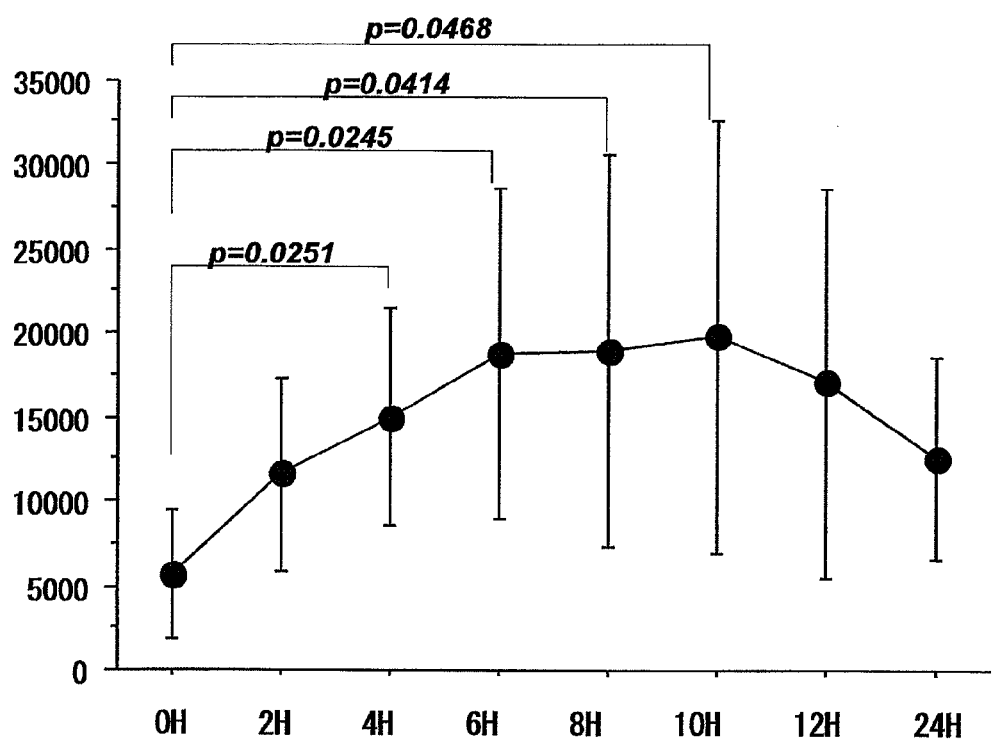
FIG. 11 shows fluctuation in the number of neutrophils in the operation.
Figure 12:
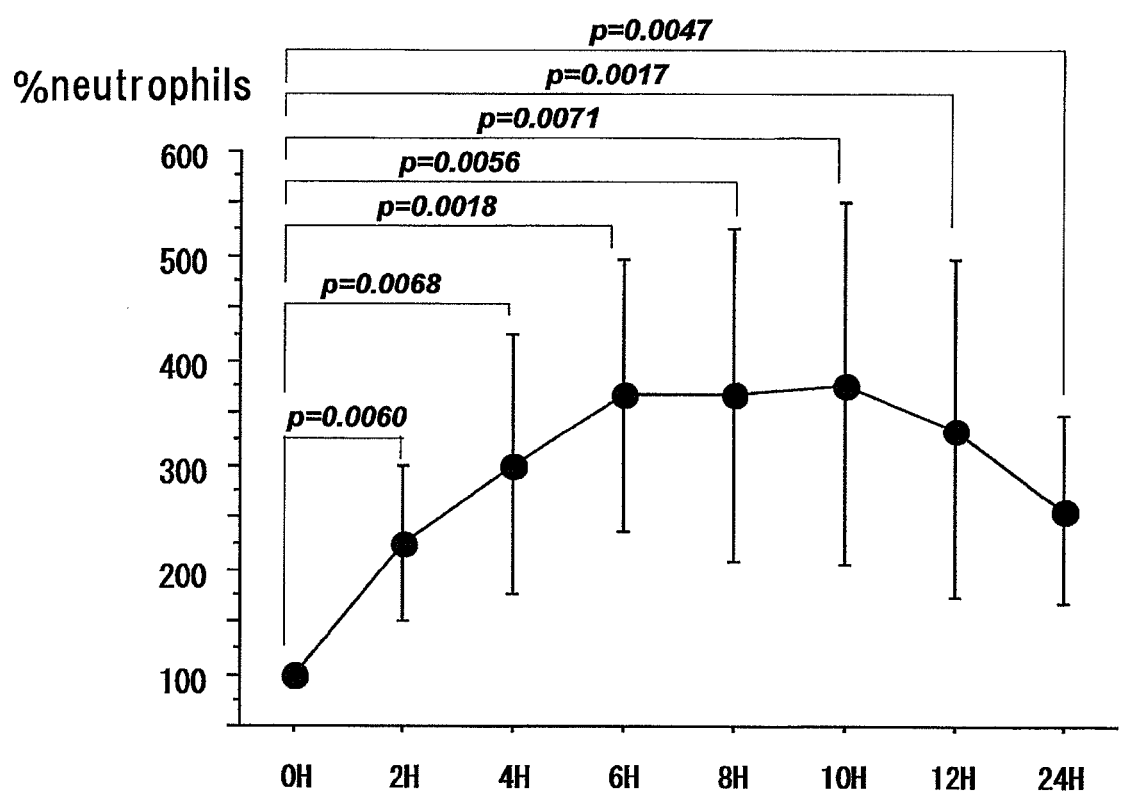
FIG. 12 shows percentage changes in the number of neutrophils in the operation.
Figure 13:
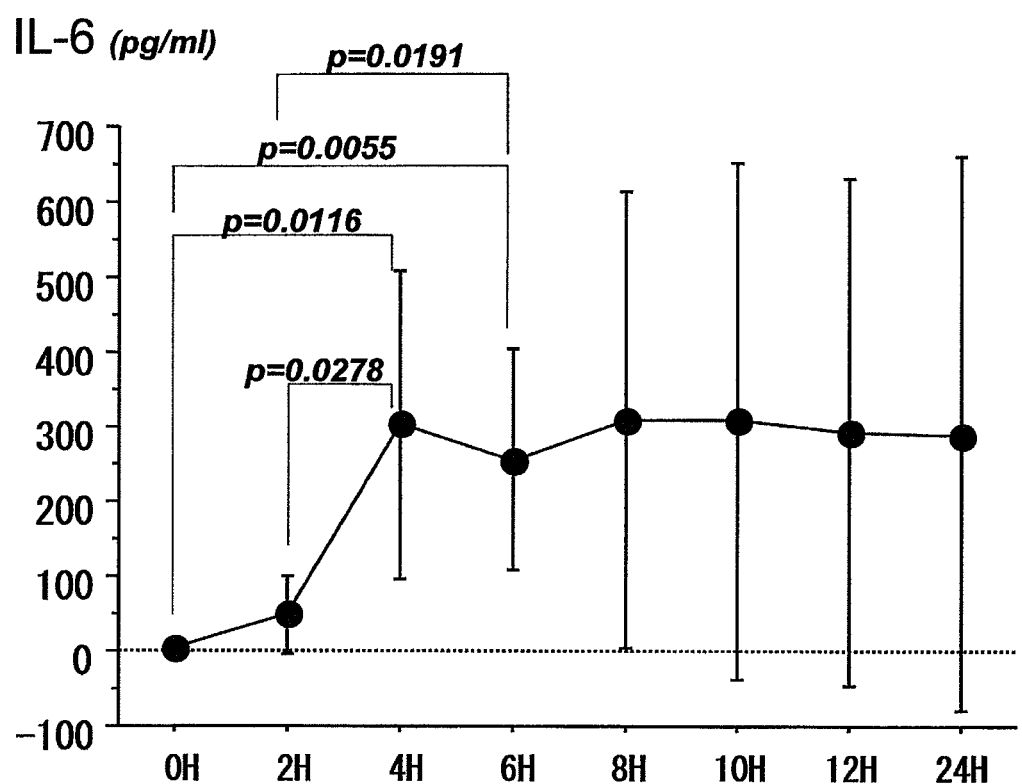
FIG. 13 shows fluctuation in blood IL-6 level in the operation.
Figure 14:
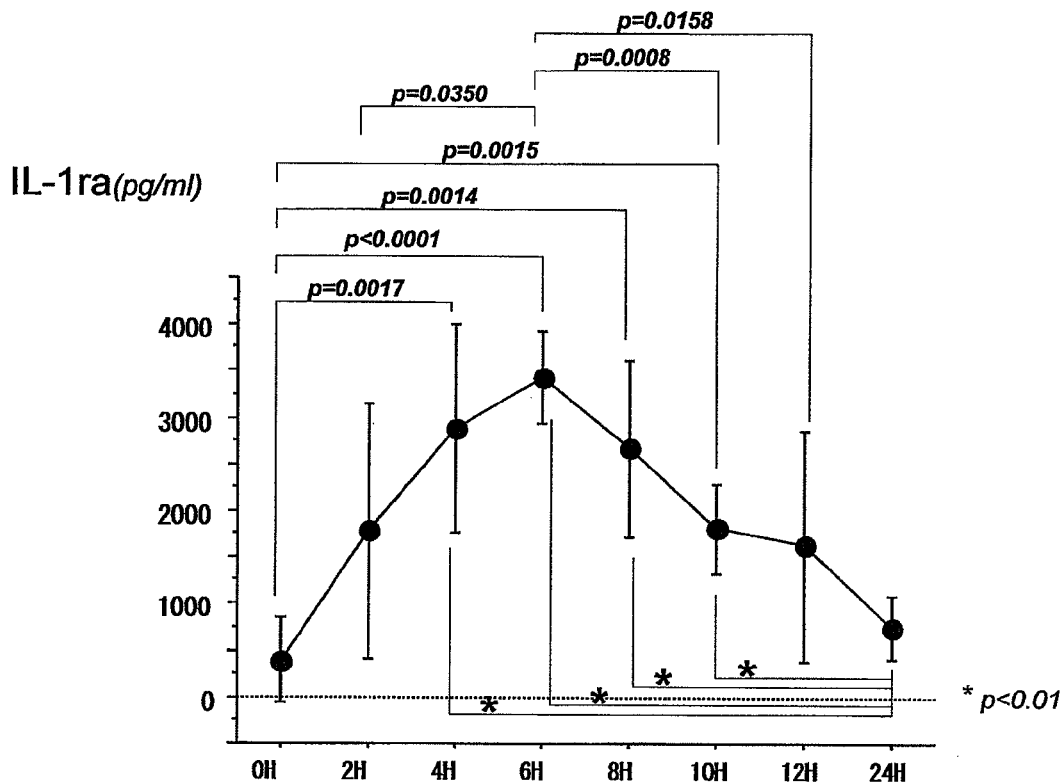
FIG. 14 shows fluctuation in blood IL-1ra level in the operation.
Figure 15:
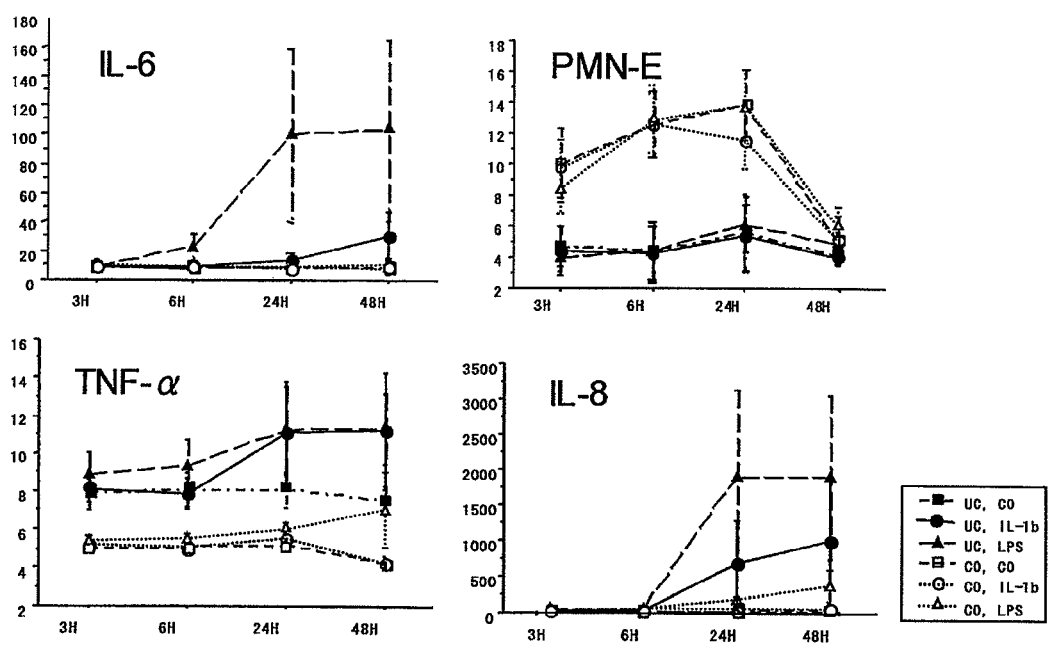
FIG. 15 shows the amounts of cytokines produced in the culture supernatants (obtained by culturing of peripheral blood neutrophils) as measured with time.
Figure 16:
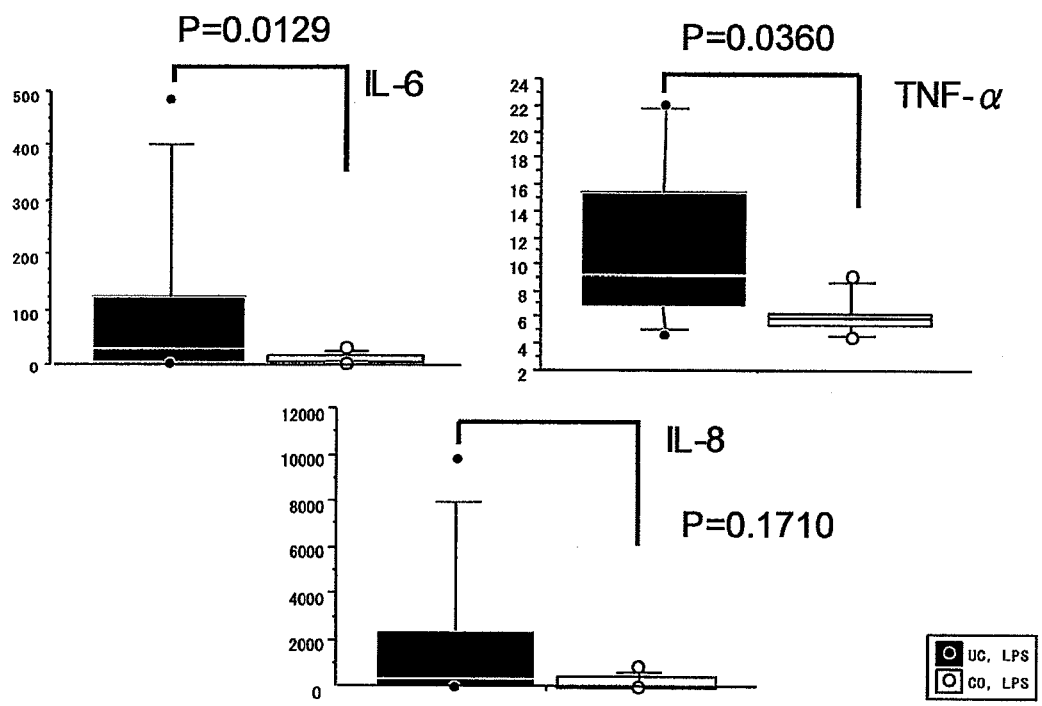
FIG. 16 shows comparison of the amounts of cytokines produced in the culture supernatants obtained by 24 hours of culturing of peripheral blood neutrophils.
Figure 17:
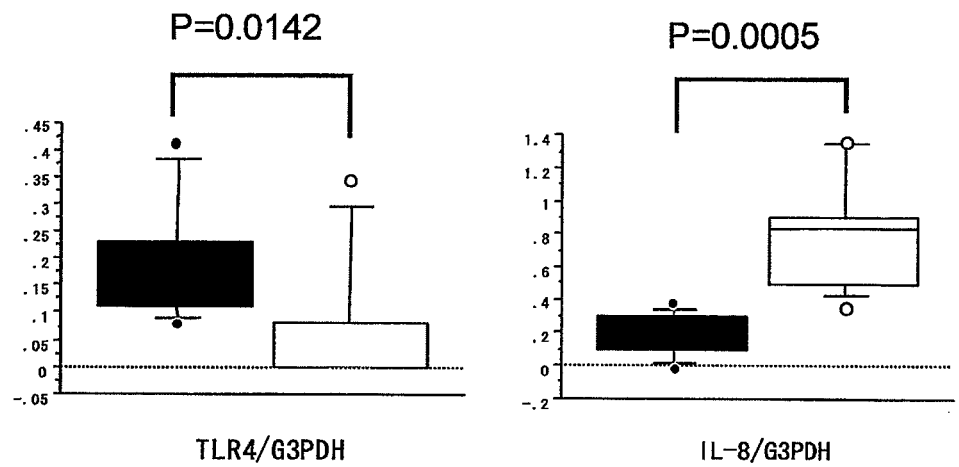
FIG. 17 shows comparison of TLR4 with IL-8 in peripheral blood neutrophils in terms of mRNA expression level.

The invention claimed is:

1. A blood processing method for a surgical subject, wherein leukocytes comprising neutrophils are removed from the blood of a surgical subject during or within 24 hours after surgical operation on a digestive system organ.

2. The blood processing method for a surgical subject according to claim 1, wherein the number of leukocytes that comprise neutrophils and are removed is $6 \times 10^7$ or more and $1 \times 10^9$ or less per kg of the body weight of the surgical subject.

3. The blood processing method for a surgical subject according to claim 1, wherein the digestive system organ is selected from among the esophagus, stomach, small intestine, large intestine, rectum, colon, appendix, liver, pancreas, and gallbladder.

4. The blood processing method for a surgical subject according to claim 1, wherein the surgical subject is a patient who has inflammatory bowel disease or cancer of a digestive system organ.

5. The blood processing method for a surgical subject according to claim 1, wherein leukocytes comprising neutrophils are removed during or within 2 hours after the surgical operation.

6. The blood processing method for a surgical subject according to claim 1, wherein leukocytes comprising neutrophils are removed using either a method that comprises removing leukocytes comprising neutrophils with the use of a specific gravity difference between erythrocytes and leukocytes by means of centrifuge or a method that comprises removing leukocytes comprising neutrophils with the use of a carrier having affinity for leukocytes.

7. The blood processing method for a surgical subject according to claim 1, wherein the carrier having affinity for leukocytes is selected from among a cellulose derivative containing cellulose acetate, polyester, polyolefin, poly(vinylidene fluoride), polyamide, polyimide, polyurethane, polysulfone, and polyacrylonitrile.

8. The blood processing method for a surgical subject according to claim 1, wherein leukocytes comprising neutrophils are removed during or within 6 hours after the surgical operation.

* * * * *